United States Patent [19]
Robinson et al.

[11] Patent Number: 6,027,944
[45] Date of Patent: *Feb. 22, 2000

[54] CAPILLARY-FILL BIOSENSOR DEVICE COMPRISING A CALIBRATION ZONE

[75] Inventors: Grenville Arthur Robinson, London; John Worthington Attridge, Woking; Julie Karen Deacon; Phelim Brinley Daniels, both of Hounslow; Colin Andrew Love, Maidenhead; Aileen Margaret Thomson, Stanwick, all of United Kingdom

[73] Assignee: Applied Research Systems ARS Holding NV, Netherlands

[ * ] Notice: This patent is subject to a terminal disclaimer.

[21] Appl. No.: 08/998,185

[22] Filed: Dec. 24, 1997

Related U.S. Application Data

[62] Continuation of application No. 08/309,793, Sep. 21, 1994, Pat. No. 5,726,064, which is a continuation of application No. 08/064,107, filed as application No. PCT/GB91/02058, Nov. 21, 1991, abandoned.

[30] Foreign Application Priority Data

Nov. 22, 1990 [GB] United Kingdom .................... 9025471

[51] Int. Cl.$^7$ ...................................................... G01N 33/543
[52] U.S. Cl. ........................... 436/518; 436/527; 436/529; 435/7.1; 435/7.93; 435/967; 422/56; 422/57; 422/82.07
[58] Field of Search ..................................... 436/514, 518, 436/527, 529, 808; 435/7.1, 967, 968, 975, 7.92, 7.93, 7.94, 7.95; 422/56, 57, 82.07, 82.08, 82.11

[56] References Cited

U.S. PATENT DOCUMENTS 5,726,064  3/1998  Robinson et al. ....................... 436/514

*Primary Examiner*—Christopher L. Chin
*Assistant Examiner*—Ginny Allen Portner
*Attorney, Agent, or Firm*—Ostrolenk, Faber, Gerb & Soffen, LLP

[57] ABSTRACT

A method of assay for a ligand in a sample is described in which calibration occurs within the assay. This is achieved utilizing a measurement region and one or more calibration regions. In at least one of the calibration regions a non-zero signal results, either because of the presence of a calibration reagent or as a result of a binding reaction analogous to that which takes place in the measurement region.

9 Claims, 16 Drawing Sheets

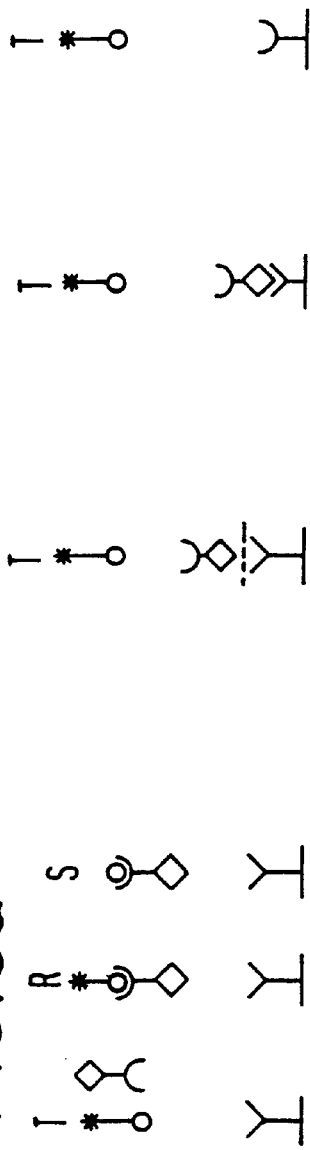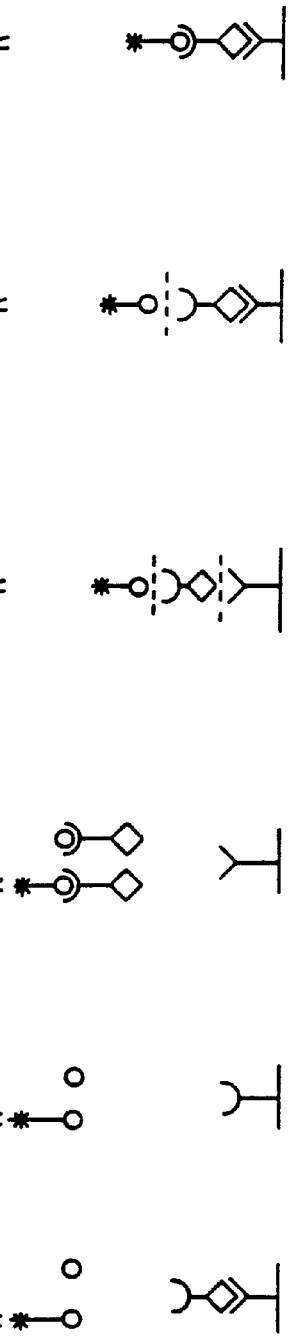

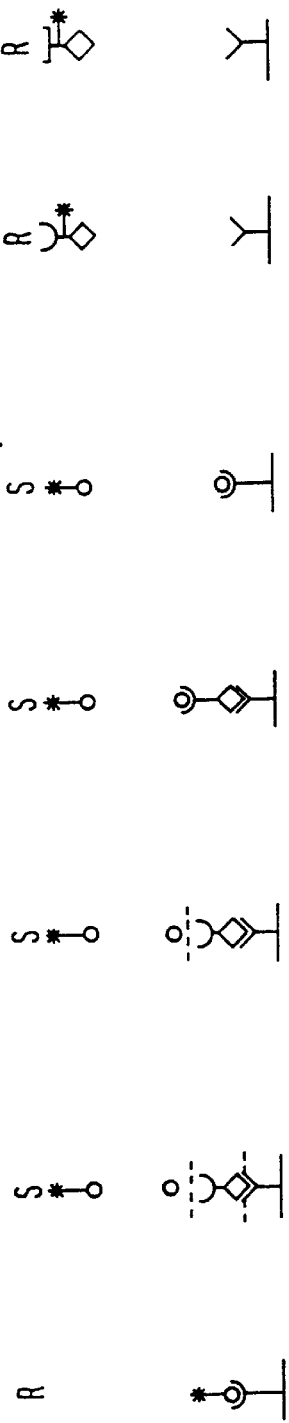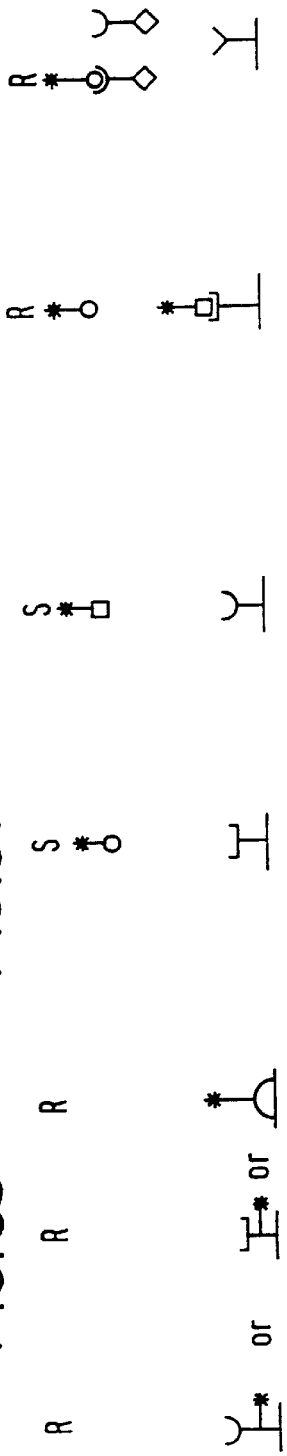

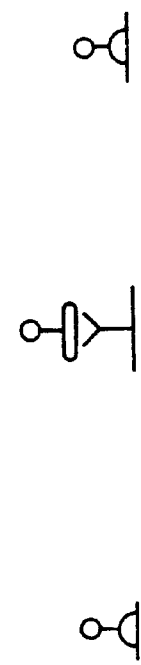
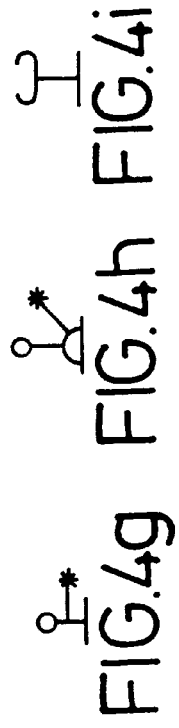
FIG.4a  FIG.4b  FIG.4c  FIG.4d  FIG.4e  FIG.4f
FIG.4g  FIG.4h  FIG.4i  FIG.4j  FIG.4k  FIG.4l FIG.4m  FIG.4n  FIG.4p  FIG.4q  FIG.4r

FIG.4s  FIG.4t

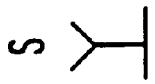
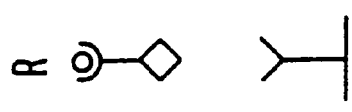
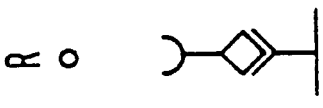
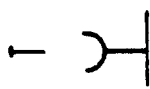

CAPILLARY-FILL BIOSENSOR DEVICE COMPRISING A CALIBRATION ZONE

This is a continuation of application Ser. No. 08/309,793, filed Sep. 21, 1994 and now U.S. Pat. No. 5,726,064 which was a continuation of application Ser. No. 08/064,107, filed May 24, 1993, now abandoned. This is also a case filed under 35 U.S.C. § 371 based on PCT application PCT/GB91/02058, filed Nov. 21, 1991 Which PCT application claims priority under 35 U.S.C. 119 based on British Application No. 9025471.5, filed Nov. 21, 1990.

This invention relates to a method of assay of chemical, biochemical or biological entities, to devices for use in such a method, to a method of manufacture of such devices and to the use of such devices.

There is now a great interest in the development of assay techniques for the detection and measurement of the presence of an analyte in a sample, and the various methods available have been extensively reviewed, for example in Biosensors: Fundamentals and Applications, edited by A. P. F. Turner, I. Karube, G. S. Wilson, Oxford Scientific Publications, 1987. Current techniques, however, are highly sensitive to temperature, reagent stability, incubation and development time, and other conditions and interfering factors which may affect the level of the signal observed. Accordingly, the precision of known assay techniques is limited by the method of calibration, which usually involves carrying out an assay on a standard sample. For example, for assays which involve an antibody, the immunological binding reactions which occur are frequently irreversible. Thus any calibration steps need to be carried out using a separate device or devices (preferably from the same manufacturing batch), which inevitably introduces errors.

The need for a separate calibration step involving the use of additional sensing devices can be avoided by using in the assay a device which is provided with appropriate reagents disposed in separate zones whereby the calibration step is effected within the assay procedure. The use of an assay method wherein a separate calibration step is effected within the assay procedure serves two main purposes, namely i) to confirm that the various reagents used in the assay procedure are performing according to their specification, and ii) to define a certain concentration level within the sample on test, and thereby to compensate for background interference (e.g. background fluorescence), temperature and pH changes and other factors originating from the sample matrix which may alter the level of the observed signals.

EP-A-0093613 (SYVA) discloses an assay method for determining the presence of an analyte in a sample by means of a measurement region and a calibration region. The method involves the use of a common species in both of the regions which gives a signal at the measurement region related to the amount of analyte in the sample, and a signal at the calibration region independent of the analyte concentration. The common species is captured in the calibration region by means of a different binding reaction to that which takes place in the measurement region.

The assay method disclosed in EP 0093613 therefore provides for a separate calibration within the assay and to a certain extent does serve purpose ii) above. However such a method of calibration suffers from a number of disadvantages. The use of a different binding reaction in the calibration region means that the behaviour of the two binding reactions (i.e. in the measurement and calibration regions respectively) will not be the same in terms of various factors e.g. susceptibility to pH and temperature, reagent stability and reagent aging. The binding reaction in the calibration region will also be affected differently by the sample matrix and so no compensation can be made for changes occurring to the signal arising from the binding reaction in the measurement region as a result of the sample matrix. There will also be no check on the performance of the binding reaction occurring in the measurement region (c.f. purpose i) above). Furthermore, the manufacture of devices for such an assay is made more complex by needing two different sets of reagents.

We have now developed an alternative assay method which overcomes these disadvantages of the method of EP 0093613 and which still fulfills the purposes i) and ii) above.

Thus, according to one aspect of the present invention we provide a method of assay for a ligand in a sample which method comprises the steps of:

i) incubating the sample, if desired together with one or more ancillary reagents, in contact with a surface ("the measurement surface") which surface carries an immobilised reagent ("the measurement reagent") appropriate to the assay technique employed whereby if ligand is present in the sample a complex involving said measurement reagent and said ligand and/or (if present) said ancillary reagent(s) is formed giving rise to a detectable signal which is a first function of the amount of ligand (if any) present in the sample;

ii) simultaneously or sequentially contacting the sample, if desired together with one or more ancillary reagents, with a further surface ("the calibration surface") onto which is immobilised a reagent ("the calibration reagent") appropriate to the assay technique employed, the calibration reagent either being such as to give rise to a non-zero signal or being such as to form a complex involving said ligand and/or said ancillary reagent(s) whereby any such complex gives rise to a non-zero signal and is formed as a result of the interaction of binding sites identical in structure to those involved in the formation of the aforesaid complex formed on the measurement surface (or, where no such complex is formed, which would be formed if ligand were present) either between the measurement reagent and the ligand or, where the ligand is not involved in said complex, between the measurement reagent and said ancillary reagent(s), the signal being either a second function of or independent of the amount of ligand (if any) present in the sample;

iii) optionally simultaneously or sequentially contacting the sample, if desired together with one or more ancillary reagents, with a further calibration surface ("the auxiliary calibration surface") onto which is immobilised a reagent ("the auxiliary calibration reagent"), the auxiliary calibration reagent being such as to give rise to a signal (zero or non-zero as herein defined) which is either a third function of or independent of the amount of ligand (if any) present in the sample; and iv) monitoring the signals arising from the measurement surface, from the calibration surface and, when present, from the auxiliary calibration surface by a method appropriate to the assay technique employed and, by comparing the signals arising from the aforesaid surfaces, thereby determining (using an appropriate algorithm to calibrate the signal arising from the measurement surface) whether and/or the extent to which the ligand under assay is present in the sample.

In the embodiments described hereinafter wherein there occurs at the calibration surface a binding reaction analogous to that which occurs at the measurement surface (if ligand is present in the sample) purpose i) indicated above is achieved i.e. there may be confirmation that the reagents in the complex which give rise to the signal have not degraded or that the binding reaction are occurring satisfactorily i.e. the binding partners in such reactions have not degraded. Purpose ii) may also be achieved in these embodiments.

In the embodiments described hereinafter wherein at the calibration surface the calibration reagent gives rise to the desired non-zero signal without there being a binding reaction to any ancillary reagent(s), purpose ii) indicated above is achieved.

The use of an optional calibration surface supplements the calibration achieved by the calibration surface. The auxiliary calibration surface may utilize similar reagents to those used in the calibration surface of may utilise reagents wherein binding reactions occur at the auxiliary calibration surface distinct from those which occur at either the measurement surface or the calibration surface, either to give a further non-zero signal or a zero-signal as defined herein.

According to a further aspect of the present invention there is provided a biosensor device suitable for use in assaying a ligand in a sample by a method of assay as hereinbefore defined, said device comprising a measurement surface carrying a measurement reagent and a calibration surface carrying a calibration reagent optionally together with one or more auxiliary calibration surfaces each carrying an auxiliary calibration reagent, said measurement reagent, calibration reagent and auxiliary calibration reagent each being as defined above.

In step ii) above, where the signal is a second function of the amount of ligand present in the sample, this second function is different to the first function specified in step i). In step iii) above, where the signal is a third function of the amount of ligand present in the sample, this third function is different to the first function specified in step i) and may be the same as, but is preferably different from, the second function specified in step ii).

Where an auxiliary calibration surface is present, the calibration reagent and auxiliary calibration reagent will be chosen such that the signals arising from the calibration surface and from the auxiliary calibration surface are not identical. Such non-identical signals can arise where the signal arising from the calibration surface and the signal arising from the auxiliary calibration surface in the sample. One example is where the calibration reagent and auxiliary calibration reagent are the same but the amounts of ancillary reagent(s) which form a complex with the calibration reagent and auxiliary calibration reagent differ. Another example is where the calibration reagent and auxiliary calibration reagent both give rise to a signal without the need for an ancillary reagent and are present in differing amounts. If it is found, despite such a choice of calibration reagent and auxiliary calibration reagent, that identical signals arise, then device failure (e.g. due to extremes of sample pH, too high a sample background signal or reagent degradation) is indicated and the assay can be rejected; this is a further advantage of the present invention.

For a qualitative method of assay for a ligand in a sample, preferably one auxiliary calibration surface is present. For a semi-quantitative method at least one auxiliary calibration surface is present. For a quantitative method, the number of auxiliary calibration surfaces present is preferably greater than one, more preferably greater than or equal to four.

BRIEF DESCRIPTION OF THE DRAWINGS

FIG. 3(a) is a diagrammatic illustration of reagent contained in regions T, R and S for a competition-type assay.

FIG. 3(b) is a diagrammatic illustration of reagent T in a first embodiment of the invention for a competition-type assay.

FIG. 3(c) is a diagrammatic illustration of reagent T in a second embodiment of the invention for a competition-type assay.

FIG. 3(d) is a diagrammatic illustration of reagent T in a third embodiment of the invention for a competition-type assay.

FIG. 3(e) is a diagrammatic illustration of region R in a first example of the invention for a competition-type assay.

FIG. 3(f) is a diagrammatic illustration of region R in a second example of the invention for a competition-type assay.

FIG. 3(g) is a diagrammatic illustration of region R in a third example of the invention for a competition-type assay.

FIG. 3(h) is a diagrammatic illustration of region R in a fourth example of the invention for a competition-type assay.

FIG. 3(i) is a diagrammatic illustration of region R in a fifth example of the invention for a competition-type assay.

FIG. 3(j) is a diagrammatic illustration of region R in a sixth example of the invention for a competition-type assay.

FIG. 3(k) is a diagrammatic illustration of region R in a seventh example of the invention for a competition-type assay.

FIG. 3(l) is a diagrammatic illustration of region S in a first example of the invention for a competition-type assay.

FIG. 3(m) is a diagrammatic illustration of region S in a second example of the invention for a competition-type assay.

FIG. 3(n) is a diagrammatic illustration of region S in a third example of the invention for a competition-type assay.

FIG. 3(p) is a diagrammatic illustration of region S in a fourth example of the invention for a competition-type assay.

FIG. 3(q) is a diagrammatic illustration of region R of a first additional example of the invention for a competition-type assay.

FIG. 3(r) is a diagrammatic illustration of region R of a second additional example of the invention for a competition-type assay.

FIG. 3(s) is a diagrammatic illustration of region R of a third additional example of the invention for a competition-type assay.

FIG. 3(t) is a diagrammatic illustration of region S in a first embodiments of the invention for a competition-type.

FIG. 3(u) is a diagrammatic illustration of region S in a first embodiments of the invention for a competition-type assay.

FIG. 3(v) is a diagrammatic illustration of region R in a further embodiment of the invention for a competition-type assay.

FIG. 3(w) is a diagrammatic illustration of region R in a further embodiment of the invention.

FIG. 3(x) is a diagrammatic illustration of region R in a further embodiment of the invention.

FIG. 4(a) diagrammatically illustrates a first example of measurement region T for a competition-type assay.

FIG. 4(b) diagrammatically illustrates a second example of measurement region T for a competition-type assay.

FIG. 4(c) diagrammatically illustrates a third example of measurement region T for a competition-type assay.

FIG. 4(d) diagrammatically illustrates a first example of a positive calibration region R for a competition-type assay.

FIG. 4(e) diagrammatically illustrates a second example of a positive calibration region R for a competition-type assay.

FIG. 4(f) diagrammatically illustrates a first example of a high signal calibration region R for a competition-type assay.

FIG. 4(g) diagrammatically illustrates a second example of a high signal calibration region R for a competition-type assay.

FIG. 4(h) diagrammatically illustrates a third example of a high signal calibration region R for a competition-type assay.

FIG. 4(i) diagrammatically illustrates a fourth example of a high signal calibration region R for a competition-type assay.

FIG. 4(j) diagrammatically illustrates a fifth example of a high signal calibration region R for a competition-type assay.

FIG. 4(k) diagrammatically illustrates a sixth example of a high signal calibration region R for a competition-type assay.

FIG. 4(l) diagrammatically illustrates a seventh example of a high signal calibration region R for a competition-type assay.

FIG. 4(m) diagrammatically illustrates a eighth example of a high signal calibration region R for a competition-type assay.

FIG. 4(n) diagrammatically illustrates a first example of a zero signal calibration region S for a competition-type assay.

FIG. 4(p) diagrammatically illustrates a second example of a zero signal calibration region S for a competition-type assay.

FIG. 4(q) diagrammatically illustrates a third example of a zero signal calibration region S for a competition-type assay.

FIG. 4(r) diagrammatically illustrates a fourth example of a zero signal calibration region S for a competition-type assay.

FIG. 4(s) diagrammatically illustrates region R for a first competition-type assay.

FIG. 4(t) diagrammatically illustrates region R for a second competition-type assay.

FIG. 5(n) diagrammatically illustrates a measurement region T.

FIG. 5(p) shows a positive calibration region R.

FIG. 5(q) shows another positive calibration region R.

FIG. 5(r) shows a high-signal calibration region R.

FIG. 5(s) shows a high-signal calibration region R.

FIG. 5(t) shows a high-signal calibration region R.

FIG. 5(u) shows a zero-signal calibration region S.

FURTHER DESCRIPTION OF THE INVENTION

Figure 1:
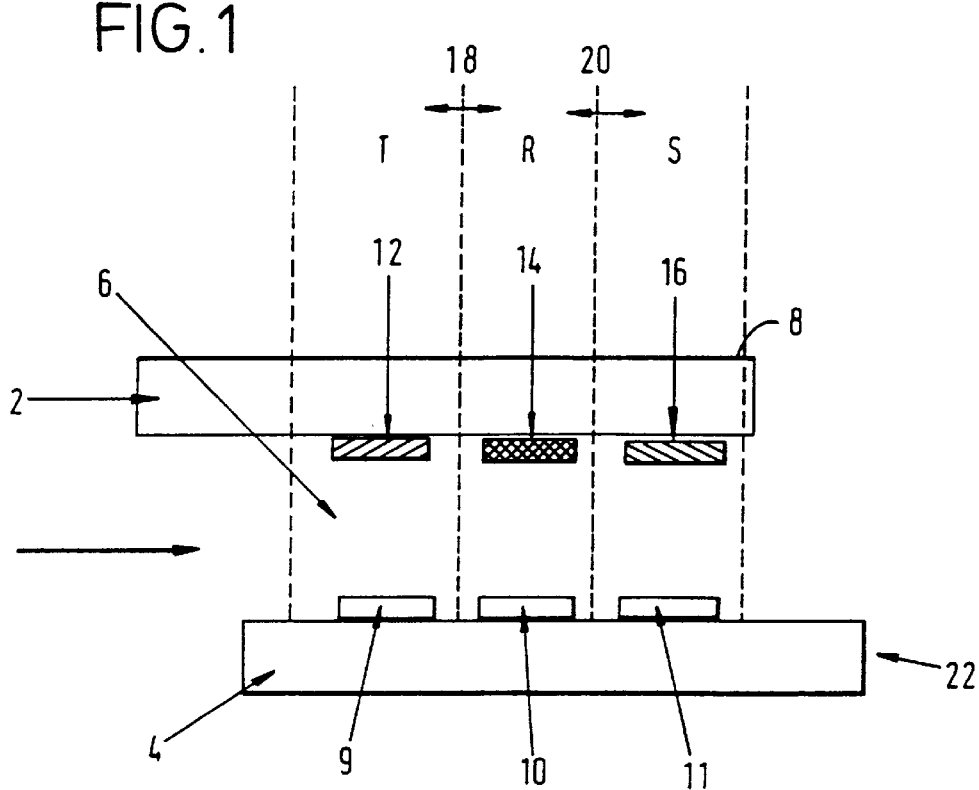
FIG. 1 is a diagrammatic section through a fluorescence capillary fill device (hereinafter FCFD).

The method of assay according to the invention is applicable to a wide variety of assay techniques including direct assays, competition assays and sandwich assays.

The term "direct assay" is used herein to mean an assay in which no ancillary reagent is required and hence in which binding of sample ligand to an appropriate specific binding partner directly modulates the signal being measured, for example certain assays using surface plasmon resonance or piezoelectric biosensors. However, such biosensors sometimes use labels to enhance their performance (for example as described in EP-A-276142). The use of such indirect assay techniques as applied to the method of the present invention is encompassed by the present application.

The term "zero signal" as used above denotes the background signal for the assay, concerned. The term "non-zero signal" is to be construed accordingly.

In a direct or sandwich assay the zero signal will be the signal obtained when no analyte is present. In a competition assay, the zero signal will be the signal corresponding to the low asymptote of the appropriate assay curve and will therefore not be the signal obtained when no analyte is present.

In direct assays, and in sandwich assays the detectable signal will in general be proportional to the quantity of ligand present in the sample. In competition assays, a complex between measurement reagent and the ancillary reagent will be formed whether or not ligand is present in the sample but the detectable signal will depend on the quantity of ancillary reagent complexed; this will in general be inversely proportional to the quantity of ligand present in the sample. The term "competition assay" as used herein includes within its scope, where the context so permits, displacement assays, e.g. assays in which the measurement reagent is pre-complexed with an appropriate ancillary reagent and this pre-complex is subsequently incubated with sample whereby at least a portion of any ligand present in the sample displaces a corresponding amount of ancillary reagent.

Thus, in one type of assay in accordance with an embodiment of the present invention:

in step i) the measurement reagent (or optionally an ancillary reagent precomplexed with or capable of forming a complex involving the measurement reagent) is a specific binding partner for the ligand under assay; and in step ii) a ligand analogue is present as an ancillary reagent and the calibration reagent (or optionally an ancillary reagent precomplexed with or capable of forming a complex involving the calibration reagent) is a specific binding partner for the ligand under assay; and in step iii) either a) the auxiliary calibration reagent and ancillary reagent(s) are equivalent to the calibration reagent and ancillary reagent(s) respectively defined in step ii) above or b) a ligand distinct from the ligand under assay is present as an ancillary reagent and the auxiliary calibration reagent (or optionally an ancillary reagent precomplexed with or capable of forming a complex involving the auxiliary calibration reagent) is a specific binding partner for the ligand distinct from the ligand under assay or c) the auxiliary calibration reagent is a binding partner non-specific for the ligand under assay.

In a competition assay according to a further embodiment of the present invention:

in step i) either a) a ligand analogue is present as an ancillary reagent and the measurement reagent (or optionally an ancillary reagent precomplexed with or capable of forming a complex involving the measurement reagent) is a specific binding partner for the ligand under assay or b) an optionally labelled specific binding partner for the ligand under assay is present as an ancillary reagent and the measurement reagent (or optionally an ancillary reagent precomplexed with or capable of forming a complex involving the measurement reagent) is a ligand analogue; and in step ii) either a) a ligand analogue is present as an ancillary reagent and the calibration reagent (or optionally an ancillary reagent precomplexed with or capable of forming a complex involving the calibration reagent) is a specific binding partner for the ligand under assay or b) an optionally labelled specific binding partner for the ligand under assay is present as an ancillary reagent and the calibration reagent (or optionally an ancillary reagent precomplexed with or capable of forming a complex involving the calibration reagent) is a ligand analogue or c) the calibration reagent gives rise to the desired non-zero signal without the need for presence of an ancillary reagent; and in step iii) either a) the auxiliary calibration reagent and ancillary reagent(s) are equivalent to the calibration reagent and ancillary reagent(s) respectively defined in step ii) above or b) an optionally labelled ligand distinct from the ligand under assay is present as an ancillary reagent and the auxiliary calibration reagent (or optionally an ancillary reagent precomplexed with or capable of forming a complex involving the auxiliary calibration reagent) is a specific binding partner for the ligand distinct from the ligand under assay or c) the auxiliary calibration reagent is a binding partner non-specific for any ancillary reagent(s) present or d) the auxiliary calibration reagent gives rise to the desired zero signal without the need for the presence of an ancillary reagent.

In a sandwich assay according to a still further embodiment of the present invention:

in step i) an optionally labelled specific binding partner for the ligand under assay is present as an ancillary reagent and the measurement reagent (or optionally an ancillary reagent precomplexed with or capable of forming a complex involving the measurement reagent) is a further specific binding partner for the ligand under assay the said further specific binding partner being directed to an epitope of the ligand under assay different to the epitope to which the optionally labelled specific binding partner is directed; and in step ii) either a) the calibration reagent (or optionally an ancillary reagent precomplexed with or capable of forming a complex involving the calibration reagent) is a specific binding partner for the ligand under assay, an optionally labelled specific binding partner for the ligand under assay is present as an ancillary reagent and a known amount of the ligand under assay precomplexed to its optionally labelled specific binding partner is present as a yet further ancillary reagent or b) an optionally labelled specific binding partner for the ligand under assay is present as an ancillary reagent and the calibration reagent (or optionally an ancillary reagent precomplexed with or capable of forming a complex involving the calibration reagent) is a known amount of the ligand under assay precomplexed to its immobilized specific binding partner or c) the calibration reagent gives rise to the desired non-zero signal without the need for presence of an ancillary reagent; and in step iii) either a) the auxiliary calibration reagent and ancillary reagent(s) are equivalent to the calibration reagent and ancillary reagent(s) respectively defined in step ii) above or b) a ligand distinct from the ligand under assay is present as an ancillary reagent and the calibration reagent (or optionally an ancillary reagent precomplexed with or capable of forming a complex involving the calibration reagent) is an optionally labelled specific binding partner for the ligand distinct from the ligand under assay or c) the auxiliary calibration reagent is an optionally labelled binding partner non-specific for any ancillary reagent(s) present or d) the auxiliary calibration reagent gives rise to the desired zero signal without the need for the presence of an ancillary reagent.

The term "ligand analogue" as used herein denotes a species which is capable of binding to the same epitopic site of the same specific binding partner as the ligand under assay, and includes inter alia within its scope a known amount of the ligand under assay or a labelled aliquot of the said ligand.

A wide variety of devices may be used to perform the method of the present invention including for example dipstick or 'test-strip' biosensors, devices using a 'sample flow-through' configuration or devices employing sample containment. Examples of biosensors which may be used in the method of the present invention include sensors involving surface plasmon resonance, piezoelectric and total internal reflectance techniques. A preferred device to carry out the method of the present invention is a capillary fill device, especially a fluorescence capillary fill device, for example the type of device described in EP-A-171148 or in WO-90/14590. Such capillary fill devices may be used singly or in a suitable holder such as described in WO-90/1830.

As described in EP-A-171148, a capillary fill device (hereinafter CFD) typically consists of two plates of transparent material, e.g. glass, separated by a narrow gap or cavity. One plate acts as an optical waveguide and carries an immobilised reagent appropriate to the test to be carried out in the device. As described in WO-90/14590, the other transparent plate can carry on its surface remote from the cavity a layer of light-absorbing or opaque material. For use in a competition assay, the immobilised reagent may for example be a specific binding partner to the ligand desired to be detected and one of the plates may carry a dissoluble reagent comprising ligand analogue, labelled with a fluorescent dye (the ancillary reagent). When a sample is presented to one end of the CFD, it is drawn into the gap by capillary action and dissolves the ancillary reagent. In a competition assay for an antigen, the fluorescently labelled antigen analogue will compete with sample antigen for the limited number of antibody binding sites immobilised on the waveguide. Because the capillary gap is narrow (typically about 100 microns), the reaction will generally go to completion in a short time, possibly less than 5 minutes depending upon the sample matrix and antibody affinity. Thus for a competition assay, the amount of fluorescently labelled antigen which becomes indirectly bound to the waveguide by virtue of complex formation will be inversely proportional to the concentration of antigen in the sample. In a sandwich assay, the waveguide will carry a specific binding partner for the ligand desired to be detected and either one of the plates will carry a dissoluble reagent comprising a further specific binding partner labelled with a fluorescent dye (the ancillary reagent). In a sandwich immunoassay for an antigen, a sample antigen will form a sandwich complex with a fluorescently labelled antibody and an antibody immobilised on the waveguide. Thus, for a sandwich immunoassay, the amount of fluorescently labelled antibody which becomes indirectly bound to the waveguide by virtue of complex formation will be directly proportional to the concentration of antigen in the sample.

The term "antigen" as used herein will be understood to include both antigenic species (for example, proteins, bacteria, bacterial fragments, cells, cell fragments and viruses) and haptens which may be rendered antigenic under suitable conditions.

According to a preferred embodiment of the device according to the invention, we provide a specifically-reactive sample-collecting and testing device for use in an assay for a ligand, possessing a cavity or cavities, one surface of the or each cavity having three zones I, II and III mutually separated and each zone carrying a layer comprising, in releasable form, a reagent suitable for the desired assay, said surface being a surface of a first solid plate fashioned of transparent material, wherein the wall of the or each cavity opposite to said first plate comprises a second plate fashioned of transparent material and adapted to act as a light-transmissive waveguide, the second plate having on its surface adjacent the cavity three zones IV, V and VI corresponding in orientation to the aforementioned zones I, II and III respectively, each of zones IV, V and VI carrying a layer comprising an immobilised reagent suitable for the desired assay. The first plate advantageously carries on its external face an opaque coating.

For convenience, in the more detailed description of such a device, the reagents carried by the aforementioned zones I, II, III, IV, V and VI will be designated as follows:

| Zone | | Reagent | |
|---|---|---|---|
| I. | (top plate) | X | (ancillary reagent in soluble, releasable form) |
| II. | (top plate) | Y | (ancillary reagent in soluble, releasable form) |
| III. | (top plate) | Z | (ancillary, reagent in soluble, releasable form) |
| IV. | (baseplate) | A | (immobilised reagent) |
| V. | (baseplate) | B | (immobilised reagent) |
| VI. | (baseplate) | C | (immobilised reagent) |

The terms "top plate" and "baseplate" are used purely for convenience of description and their use is not intended to limit in any way the configuration in which the device may be used.

The arrangement of the aforementioned zones is such that zone I is paired together with zone IV, zone II is paired together with zone V and zone III is paired together with zone VI, such that one of said pairs provides the region of the device which gives rise to a measurement of the amount of ligand it is desired to assay (the "measurement region") and the other two pairs provide regions of the device which give rise to measurements which can be used as control or calibration parameters (the "calibration regions").

CFDs for use in the method of the invention may if desired contain more than one auxiliary calibration zone; and may if desired contain multiple assay zones enabling simultaneous or sequential assays for different ligands in the same sample to be conducted. For example, the device could contain a first measurement zone and a calibration zone as herein defined for one assay together with a further measurement zone for a different assay. The calibration zone would also serve as a calibration for the further measurement zone although such calibration would differ from that for the first measurement zone. Additionally, auxiliary calibration zones could be included as desired.

The identities of the reagents X, Y, Z, A, B and C will depend both on the ligand it is desired to assay and on the assay methodology. The reagents carried in the zones on the first transparent plate may be contained within a dissoluble layer of a suitable material. After deposition of the soluble reagent, a capping layer e.g. polyvinyl alcohol (PVA) may be placed upon the reagent, which capping layer delays the dissolution of the reagent for a few seconds after the addition of the sample to the device. This is to prevent the reagents being washed from one zone to another thereby precluding an accurate assay. The cavity or cavities of the device are preferably of a dimension small enough to enable sample liquid to be drawn into the cavity by capillary action, although any other method of filling said cavities may be employed. The zones on the first transparent plate and thereby the corresponding zones on the second transparent plate may be arranged either in tandem or in any other geometrical arrangement which maintains the integrity of the zones.

In a first embodiment of the device suitable for use in a direct assay, the reagent X may be absent; the reagent Y may be a known amount of the ligand under assay, and the reagent Z may be absent. In this embodiment reagent A may be a reactive species immobilised on the surface of the plate being a specific binding partner for the ligand under assay; reagent B may be identical to reagent A; and reagent C may be a reactive species immobilised on the surface of the plate being a binding partner non-specific for the ligand under assay.

In a second embodiment of the device suitable for use in a direct assay, the reagent X may be absent. In such an embodiment, the reagent Y may be a known amount of the ligand under assay together with an amount of a specific binding partner for the ligand under assay such that a fully saturated complex exists. In such an embodiment, the reagent Z may be absent. Thus, zone II carries a known amount of a ligand bound to its specific binding partner. Reagent A may be a reactive species immobilised on the surface of the plate being a specific binding partner for the ligand under assay; reagent B may be a reactive species immobilised on the surface of the plate being a specific binding partner for the reagent Y; and reagent C may be a reactive species immobilised on the surface of the plate being a binding partner non-specific for the ligand under assay.

In a first embodiment of the device suitable for use in a competition type assay, the reagent X may be a fluorescently labelled ligand analogue together with a known amount of a specific binding partner for the sample ligand under assay. In such an embodiment, the reagent Y may be a fluorescently labelled ligand analogue together with an amount of a specific binding partner for the sample ligand under assay such that a fully saturated complex exists. In such an embodiment, the reagent Z may be a known amount of ligand under assay together with an amount of a specific binding partner for the ligand under assay such that a fully saturated complex exists. Thus zone I carries a known amount of both fluorescently labelled ligand analogue and its specific binding partner; zone II carries a known amount of a fluorescently labelled ligand analogue bound to its specific binding partner; whilst zone III carries a known amount of the ligand under assay bound to its specific binding partner; reagent A may be a reactive species immobilised on the surface of the plate, being a specific binding partner for the specific binding partner of the sample ligand under assay; and both reagent B and reagent C may be equivalent to reagent A.

In a second embodiment of the device suitable for use in a competition type assay, the reagent X may be a fluorescently labelled ligand analogue; the reagent Y may be the reagent X together with a known amount of ligand itself; and the reagent Z may be a fluorescently labelled ligand analogue together with an amount of a specific binding partner for the sample ligand under assay such that a fully saturated complex exists. Thus zone I carries a known amount of a fluorescently labelled ligand analogue; zone II carries known amounts of both fluorescently labelled ligand analogue and the ligand under assay; whilst zone III carries a known amount of a fluorescently labelled ligand analogue bound to its specific binding partner. Reagent A may be a reactive species immobilised on the surface of the plate, being a specific binding partner for the sample ligand under assay; reagent B may be equivalent to reagent A; and reagent C may be a reactive species immobilised on the surface of the plate, being a specific binding partner for the specific binding partner of the sample ligand under assay.

In a third embodiment of the device suitable for use in a competition type assay, the reagent X may be a fluorescently labelled ligand analogue. In such an embodiment, the reagent Y may be absent and the reagent Z may be equivalent to the reagent X. Thus zone I and zone III both carry a known amount of fluorescently labelled ligand analogue. Reagent A may be a reactive species immobilised on the surface of the plate, being a specific binding partner for the sample ligand under assay; reagent B may be a reactive species immobilised on the surface of the plate, being a fluorescently labelled binding partner which may be either specific or non-specific for the sample ligand under assay; and reagent C may be a reactive species immobilised on the surface of the plate, being a binding partner non-specific for the sample ligand under assay.

In a fourth embodiment of the device suitable for use in a competition type assay, the reagent X may be a fluorescently labelled ligand analogue. In such an embodiment, the reagent Y may be a fluorescently labelled ligand analogue together with an amount of a specific binding partner for the sample ligand under assay such that a fully saturated complex exists. In such an embodiment, the reagent Z may be the ligand under assay together with an amount of a specific binding partner for the ligand under assay such that a fully saturated complex exists. Thus zone I carries a known amount of both fluorescently labelled ligand analogue and its specific binding partner; zone II carries a known amount of a fluorescently labelled ligand analogue bound to its specific binding partner; whilst zone III carries a known amount of the ligand under assay bound to its specific binding partner. Reagent A may be a reactive species immobilised on the surface of the plate, being a specific binding partner for the sample ligand under assay; and both reagent B and reagent C may be equivalent to reagent A.

In a fifth embodiment of the device suitable for use in a competition-type assay, the reagent X may be a fluorescently labelled ligand analogue. In such an embodiment, reagent Y may be absent and the reagent Z may be absent or may be equivalent to reagent X. Thus zone I and optionally zone III both carry a known amount of a fluorescently labelled ligand analogue. Reagent A may be a reactive species immobilized on the surface of the plate, being a specific binding partner for the sample ligand under assay; reagent B may be the same as reagent A but together with an amount of reagent X such that either a fully saturated complex of reagent A with reagent X exists or that said complex forms under the operation of the assay; and reagent C may be same as reagent A but together with an amount of the sample ligand under assay such that either a fully saturated complex of reagent A with the sample ligand under assay exists or that said complex forms under the operation of the assay and when reagent Z is present, additionally reagent A together with an amount of a fluorescently labelled ligand analogue such that either a fully saturated complex of reagent A with the ligand analogue exists or that said complex forms under the operation of the assay is present.

In a sixth embodiment of the device suitable for use in a competition type assay, the reagent X may be a fluorescently labelled ligand analogue. In such an embodiment, the reagent Y may be a fluorescently labelled ligand analogue together with an amount of a specific binding partner for the sample ligand under assay such that a fully saturated complex exists and the ligand under assay together with an amount of a specific binding partner for the sample ligand under assay such that a fully saturated complex exists. In such an embodiment, reagent Z may be equivalent to reagent X. Thus, zone I carries a known amount of fluorescently labelled ligand analogue; zone II carries a known amount of a fluorescently labelled ligand analogue bound to its specific binding partner together with a known amount of the ligand under assay bound to its specific binding partner; whilst zone III carries the same reagent as zone I. Reagent A may be a reactive species immobilised on the surface of the plate, being a specific binding partner for the sample ligand under assay; reagent B may be a reactive species immobilised on the surface of the plate, being a specific binding partner for the specific binding partner of the sample ligand under assay; and reagent C may be a reactive species immobilised on the surface of the plate, being a binding partner non-specific for the sample ligand under assay.

The measurement regions and some of the calibration regions in the embodiments hereinbefore described are such that the species which becomes bound to the immobilised reagent on the measurement or calibration surface is bound indirectly via one intervening moiety. Further embodiments wherein no intervening moiety is present and those wherein more than one intervening moiety is present suggest themselves and are equally within the scope of the present invention. The following fourteen embodiments relate to the case where no intervening moiety is present i.e. the species becomes bound directly to the immobilised reagent on the measurement or calibration surface.

In a seventh embodiment of the device suitable for use in a competition type assay, the reagent X may be a fluorescently labelled ligand analogue. In such an embodiment, the reagent Y may be the reagent X together with the ligand itself and the reagent Z may be equivalent to the reagent X or may be absent. Thus, zone I carries a known amount of a fluorescently labelled ligand analogue; zone II carries known amounts of both fluorescently labelled ligand analogue and the ligand under assay; whilst when reagent Z is present zone III carries the same reagent as zone I. In such an embodiment, reagent A may be a reactive species immobilised on the surface of the plate, being a specific binding partner for the sample ligand under assay; reagent B may be equivalent to reagent A; and reagent C may be reagent A together with an amount of reagent X such that either a fully saturated complex of reagent a with reagent X exists or that said complex forms under the operation of the assay.

In an eighth embodiment of the device suitable for use in a competition-type assay, the reagent X may be a fluorescently labelled ligand analogue. In such an embodiment, the reagent Y may be the same as reagent X but together with the ligand itself and the reagent Z may be equivalent to the reagent X. Thus zone I carries a known amount of a fluorescently labelled ligand analogue; zone II carries known amounts of both fluorescently labelled ligand analogue and the ligand under assay; whilst zone III carries the same reagent as zone I; reagent A may be a reactive species immobilized on the surface of the plate, being a specific binding partner for the sample ligand under assay; reagent B may be equivalent to reagent A; and reagent C may be reagent A together with an amount of the sample ligand under assay such that either a fully saturated complex of reagent A with the sample ligand under assay exists or that said complex forms under the operation of the assay.

In a ninth embodiment of the device suitable for use in a competition type assay, the reagent X may be a fluorescently labelled ligand analogue. In such an embodiment, the reagent Y may be same as the reagent X but together with the ligand itself and the reagent Z may be equivalent to the reagent X. Thus, zone I carries a known amount of a fluorescently labelled ligand analogue; zone II carries known amounts of both fluorescently labelled ligand analogue and the ligand under assay; whilst zone III carries the same reagent as zone I; reagent A may be a reactive species immobilized on the surface of the plate, being a specific binding partner for the sample ligand under assay; and reagent B may be equivalent to reagent A; and reagent C may be a reactive species immobilized on the surface of the plate, being a specific binding partner for a ligand other than the sample ligand under assay, optionally together with an amount of the ligand for which it is a specific binding partner such that a fully saturated complex of said reaction species with its specific binding partner exists or that said complex forms under the operation of the assay.

In a tenth embodiment of the device suitable for use in a competition type assay, the reagent X may be a fluorescently labelled ligand analogue. In such an embodiment, the reagent Y may be the same as reagent X but together with the ligand itself and the reagent Z may be equivalent to the reagent X. Thus, zone I carries a known amount of a fluorescently labelled ligand analogue; zone II carries known amounts of both fluorescently labelled ligand analogue and the ligand under assay; whilst zone III carries the same reagent as zone I; reagent A may be a reactive species immobilized on the surface of the plate, being a specific binding partner for the sample ligand under assay; and reagent B may be equivalent to reagent A; and reagent C may be a reactive species immobilized on the surface of the plate, being a specific binding partner for a ligand other than the sample ligand under assay, optionally together with an amount of a fluorescently labelled analogue of a ligand for which it is a specific binding partner such that either a fully saturated complex of said reactive species with said analogue of the ligand that is its specific binding partner exists or that said complex forms under the operation of the assay.

In an eleventh embodiment of the device suitable for use in a competition-type assay, the reagent X may be a fluorescently labelled ligand analogue. In such an embodiment, the reagent Y may be same as the reagent X but together with the ligand itself. In such an embodiment, the reagent Z may be a ligand analogue, said ligand being distinct from the sample ligand and not being a specific binding partner for the reactive species for which the sample ligand is a specific binding partner. Thus zone I carries a known amount of a fluorescently labelled ligand analogue; zone II carries known amounts of both the fluorescently labelled ligand analogue and the ligand under assay; whilst zone III carries a known amount of a fluorescently labelled ligand analogue distinct from the ligand analogue used in zone I; reagent A may be a reactive species immobilized on the surface of the plate, being a specific binding partner for the sample ligand under assay; and both reagent B and reagent C may be equivalent to reagent A.

In a twelfth embodiment of the device suitable for use in a competition-type assay, the reagent X may be a fluorescently labelled ligand analogue. In such an embodiment, both the reagent Y and the reagent Z may be equivalent to reagent X. Thus all three zones I, II and III carry a known amount of a fluorescently labelled ligand analogue; reagent A may be a reactive species immobilised on the surface of the plate, being a specific binding partner for the sample ligand under assay; reagent B may be the same as reagent A but together with an amount of reagent X such that either a fully saturated preformed complex of reagent A with reagent X exists or that said complex forms under the operation of the assay; and reagent C may be a reactive species immobilised on the surface of the plate, being a specific binding partner for a ligand other than the sample ligand under assay, optionally together with an amount of the ligand for which it is a specific binding partner such that a fully saturated complex of said reactive species with its specific binding partner exists or that said complex forms under the operation of the assay.

In a thirteenth embodiment of the device suitable for use in a competition-type assay, the reagent X may be a fluorescently labelled ligand analogue. In such an embodiment, the reagent Y may be equivalent to the reagent X. In such an embodiment, the reagent Z may be a fluorescently labelled ligand analogue, said ligand being distinct from the sample ligand and being a binding partner non-specific for the reactive species for which the sample ligand is a specific binding partner. Thus zone I and zone II both carry a known amount of a fluorescently labelled ligand analogue; whilst zone III carries a known amount of a fluorescently labelled ligand analogue distinct from the ligand analogue used in zone I; reagent A may be a reactive species immobilized on the surface of the plate, being a specific binding partner for the sample ligand under assay; reagent B may be the same as reagent A but together with an amount of reagent X such that either a fully saturated complex of reagent A with reagent X exists or that said complex forms under the operation of the assay; and reagent C may be the same as reagent A optionally together with an amount of the sample ligand under assay such that either a fully saturated complex of reagent A with the sample ligand under assay exists or that said complex forms under the operation of the assay.

In a fourteenth embodiment of the device suitable for use in a competition-type assay, the reagent X may be a fluorescently labelled ligand analogue. In such an embodiment, the reagent Y may be absent or may be equivalent to reagent X and the reagent Z may be equivalent to reagent X. Thus zones I and III and optionally zone II carry a known amount of a fluorescently labelled ligand analogue; reagent A may be a reactive species immobilized on the surface of the plate, being a specific binding partner for the sample ligand under assay; reagent B may be a fluorescently labelled reactive species immobilized on the surface of the plate, optionally being a specific binding partner for the sample ligand under assay; and reagent C may be reagent A together with an amount of the sample ligand under assay such that either a fully saturated complex of reagent with the sample ligand under assay exists or that said complex forms under the operation of the assay.

In a fifteenth embodiment of the device suitable for use in a competition-type assay, the reagent X may be a fluorescently labelled ligand analogue. In such an embodiment, the reagent Y may be absent and the reagent Z may be equivalent to reagent X. Thus zones I and III carry a known amount of a fluorescently labelled ligand analogue; reagent A may be a reactive species immobilized on the surface of the plate, being a specific binding partner for the sample ligand under assay; reagent B may be a fluorescently labelled reactive species immobilized on the surface of the plate, optionally being a specific binding partner for the sample ligand under assay; and reagent C may be a reactive species immobilized on the surface of the plate, being a specific binding partner for a ligand other than the sample ligand under assay, optionally together with an amount of the ligand for which it is a specific binding partner such that either a fully saturated complex of said reactive species with the ligand that is its specific binding partner exists or that said complex forms under the operation of the assay.

In a sixteenth embodiment of the device suitable for use in a competition-type assay, the reagent X may be a fluorescently labelled ligand analogue. In such an embodiment, the reagent Y may be the same as reagent X but together with the ligand under assay. In such an embodiment, the reagent Z may be the reagent X together with an amount of the ligand under assay, said amount being different to that present in reagent Y. Thus zone I carries a known amount of a fluorescently labelled ligand analogue; both zone II and zone III carry known amounts of both fluorescently labelled ligand analogue and the ligand under assay; reagent A may be a reactive species immobilized on the surface of the plate, being a specific binding partner for the sample ligand under assay; and both reagent B and reagent C may be equivalent to reagent A.

In a seventeenth embodiment of the device suitable for use in a competition type assay, the reagent X may be a fluorescently labeled specific binding partner for the ligand under assay. In such an embodiment, the reagent Y may be a fluorescently labelled specific binding partner for the ligand under assay and a fluorescently labelled specific binding partner for the ligand under assay together with an amount of the ligand under assay such that a fully saturated complex exists. In such an embodiment, the reagent Z may be a fluorescently labelled binding partner non-specific for the ligand under assay. Thus, zone I carries a known amount of fluorescently labelled specific binding partner for the ligand under assay; zone II carries a known amount of fluorescently labelled specific binding partner for the ligand under assay bound to the ligand under assay together with a known amount of the unlabelled specific binding partner for the ligand under assay; whilst zone III carries a known amount of a fluorescently labelled binding partner non-specific for the ligand under assay; reagent A may be a reactive species immobilised on the surface of the plate, being the ligand under assay; and reagent B and reagent C may be identical to reagent A.

In an eighteenth embodiment of the device suitable for use in a competition type assay, the reagent X may be a fluorescently labelled specific binding partner for the ligand under assay. In such an embodiment, the reagent Y may be absent. In such an embodiment, the reagent Z may be a fluorescently labelled specific binding partner for the ligand under assay together with an amount of the ligand under assay such that a fully saturated complex exists and a fluorescently labelled ligand analogue, said ligand not being the ligand under assay. Thus, zone I carries a known amount of fluorescently labelled specific binding partner for the ligand under assay; whilst zone III carries a known amount of unlabelled specific binding partner for the ligand under assay bound to the ligand under assay together with a fluorescently labelled ligand analogue, the ligand being distinct from the ligand under assay; reagent A may be a reactive species immobilised on the surface of the plate, being the ligand under assay; and reagent B may be a reactive species immobilised on the surface of the plate, being a fluorescently labelled ligand analogue; and reagent C may be a reactive species immobilised on the surface of the plate, being a specific binding partner for the ligand under assay.

In a nineteenth embodiment of the device suitable for use in a competition type assay, the reagent X may be a fluorescently labelled specific binding partner for the ligand under assay. In such an embodiment, the reagent Y may be a known amount of the ligand under assay together with its specific binding partner such that a fully saturated complex exists at a specific ration (e.g. 1:2). In such an embodiment, the reagent Z may be a fluorescently labelled binding partner non-specific for the ligand under assay. Thus zone I carries a known amount of fluorescently labelled specific binding partner for the ligand under assay; zone II carries a known amount of fluorescently labelled specific binding partner for the ligand under assay bound to the ligand under assay; whilst zone III carries a known amount of a fluorescently labelled binding partner non-specific for the ligand under assay; reagent A may be a reactive species immobilised on the surface of the plate, being the ligand under assay; and reagent B may either be a reactive species immobilised on the surface of the plate, being a specific binding partner for the ligand under assay or may be equivalent to reagent A; and reagent C may be equivalent to reagent A.

In a twentieth embodiment of the device suitable for use in a competition type assay, the reagent X may be a fluorescently labelled specific binding partner for the ligand under assay. In such an embodiment, the reagent Y may be absent. In such an embodiment, the reagent Z may be a fluorescently labelled binding partner non-specific for the ligand under assay. Thus zone I carries a known amount of fluorescently labelled specific binding partner for the ligand under assay; whilst zone III carries a known amount of a fluorescently labelled binding partner non-specific for the ligand under assay; reagent A may be a reactive species immobilised on the surface of the plate, being the ligand under assay; and reagent B may be a reactive species immobilised on the surface of the plate, being the ligand under assay, together with a fluorescently labelled specific binding partner for the ligand under assay such that either a performed complex of the ligand under assay with its specific binding partner exists or that said complex forms under the operation of the device; and reagent C may be identical to reagent A.

In the above embodiments of devices suitable for use in competition assays, where one of the reagents is a fluorescently labelled ligand analogue this may conveniently be a fluorescently labelled aliquot of the ligand under assay.

In a first embodiment of the device suitable for use in a sandwich-type assay, the reagent X may be a fluorescently labelled specific binding partner for the ligand under assay, whilst reagent Y may be a fully saturated complex of reagent X and a known amount of the ligand itself. In such an embodiment, the reagent Z may be a fluorescently labelled binding partner non-specific for the ligand under assay. Thus, zone I carries a known amount of a fluorescently labelled specific binding partner; zone II carries a known amount of the fluorescently labelled specific binding partner bound to the ligand under assay; whilst zone III carries a known quantity of a binding partner non-specific for the ligand under assay carrying the same fluorescent label as reagent X; reagent A may be a reactive species immobilized on the surface of the plate, being a specific binding partner for the sample ligand under assay; and both reagent B and reagent C may be identical to reagent A.

In a second embodiment of the device suitable for use in a sandwich-type assay, the reagent X may be a fluorescently labelled specific binding partner to the ligand under assay, whilst reagent Y may be a fully saturated complex of reagent X and a known amount of the ligand itself. In such an embodiment, the reagent Z may be identical to the reagent X. Thus zone I carries a known amount of a fluorescently labelled specific binding partner to the ligand under assay; zone II carries a known amount of the fluorescently labelled specific binding partner bound to the ligand under assay; whilst zone III carries the same reagent as zone I; reagent A may be a reactive species immobilized on the surface of the plate, being a specific binding partner for the sample ligand under assay; and reagent B may be identical to reagent A; and reagent C may be a reactive species immobilized on a surface of the plate, being a specific binding partner for a ligand other than the sample ligand under assay, optionally together with an amount of ligand for which it is a specific binding partner such that either a fully saturated complex of said reactive species with the ligand that is its specific binding partner exists or that said complex forms under the operation of the assay.

In a third embodiment of the device suitable for use in a sandwich-type assay, the reagent X may be a fluorescently labelled specific binding partner to the ligand under assay. In such an embodiment, the reagent Y may be absent. In such an embodiment, the reagent Z may be a fluorescently labelled specific binding partner for the ligand under assay together with the ligand under assay in a fully saturated complex. Thus, zone I carries a known amount of a fluorescently labelled specific binding partner for the ligand under assay; whilst zone III carries a known amount of the fluorescently labelled specific biding partner bound to the ligand under assay; reagent Z may be a reactive species immobilised on the surface of the plate, being a specific binding partner for the ligand under assay; reagent B may be a fluorescently labelled reactive species is immobilised on the surface of the plate, optionally a specific binding partner for the sample ligand under assay; and reagent C may be reagent A together with an amount of the ligand under assay such that a full saturated complex exists.

In a fourth embodiment of the device suitable for use in a sandwich-type assay, the reagent X may be a fluorescently labelled specific binding partner to the ligand under assay. In such an embodiment, the reagent Y may be absent. In such an embodiment, the reagent Z may be a fluorescently labelled binding partner non-specific for the ligand under assay. Thus, zone I carries a known amount of a fluorescently labelled specific binding partner for the ligand under assay; whilst zone III carries a known quantity of a fluorescently-labelled binding partner non-specific for the ligand under assay; reagent A may be a reactive species immobilised on the surface of the plate, being a specific binding partner for the ligand under assay; reagent B may be a fluorescently labelled reactive species immobilised on the surface of the plate, optionally a specific binding partner for the sample ligand under assay; and reagent C may be identical to reagent A.

In a fifth embodiment of the device suitable for use in a sandwich-type assay, the reagent X may be a fluorescently labelled specific binding partner to the ligand under assay. In such an embodiment, the reagent Y may be a fluorescently labelled specific binding partner for the ligand under assay together with an amount of the ligand under assay such that a fully saturated complex exists and a further fluorescently labelled specific binding partner for the ligand under assay. In such an embodiment, the reagent Z may be a fluorescently labelled binding partner non-specific for the ligand under assay. Thus, zone I carries a known amount of a fluorexcently labelled specific binding partner for the ligand under assay; zone II carries a known amount of a fluorescently-labelled specific binding partner bound to the ligand under assay together with a known amount of the fluorescently labelled specific binding partner for the ligand under assay; whilst zone III carries a known quantity of a fluorescently-labelled binding partner non-specific for the ligand under assay; reagent A may be a reactive species immobilised on the surface of the plate, being a specific binding partner for the ligand under assay; and reagent B and reagent C may both be identical to reagent A.

In a sixth embodiment of the device suitable for use in a sandwich-type assay, the reagent X may be a fluorescently labelled specific binding partner to the ligand under assay. In such an embodiment, the reagent Y may be a fluorescently labelled specific binding partner for the ligand under assay together with an amount of the ligand under assay in a fully saturated complex and a further specific binding partner for the ligand under assay together with an amount of the ligand under assay in a fully saturated complex. In such an embodiment, the reagent Z may be a fluorescently labelled binding partner non-specific for the ligand under assay. Thus, zone I carries a known amount of a fluorescently labelled specific binding partner for the ligand under assay; zone II carries a known amount of fluorescently-labelled specific binding partner bound to the ligand under assay together with a known amount of unlabelled specific binding partner bound to the ligand under assay; whilst zone III carries a known quantity of a fluorescently-labelled binding partner non-specific for the ligand under assay; reagent Z may be a reactive species immobilised on the surface of the plate, being a specific binding partner for the ligand under assay; and reagent B and reagent C may both be identical to reagent A.

In a seventh embodiment of the device suitable for use in a sandwich-type assay, the reagent X may be a fluorescently labelled specific binding partner to the ligand under assay. In such an embodiment, the reagent Y may be absent. In such an embodiment, the reagent Z may be a fluorescently labelled binding partner non-specific for the ligand under assay. Thus, zone I carries a known amount of a fluorescently labelled specific binding partner for the ligand under assay; whilst zone III carries a known quantity of a fluorescently-labelled binding partner non-specific for the ligand under assay; reagent A may be a reactive species immobilised on the surface of the plate, being a specific binding partner for the ligand under assay; and reagent B may be a reactive species immobilised on the surface of the plate being a specific binding partner for the ligand under assay together with an amount of the ligand under assay and an amount of a fluorescently labelled specific binding partner for the ligand under assay such that a fully saturated complex exists or that said complex forms under the operation of the assay; and reagent C may be identical to reagent A.

The reasons for using the reagents X, Y, Z, A, B and C described for the various embodiments will be discussed later.

In the embodiments of the device hereinbefore described, in the case where the ligand under assay is unstable in solution or is rare, expensive or difficult to prepare in a sufficiently pure and/or quantifiable form, in the calibration region(s), wherein the ligand under assay is used as a calibration reagent, this ligand may be replaced by a calibrator as described in EP-A-343932.

Capillary fill devices according to the invention may be manufactured by methods broadly similar to those described in EP-A-171148.

Thus, according to the present invention we also provide a method of manufacturing specifically-reactive sample-collecting and testing devices as described hereinbefore comprising the steps of (a) forming an array of patches of suitable reagents, carried by zones I, II and III as described hereinbefore on the surface of a sheet material which is to provide part of a multiplicity of the devices, (b) forming an array of patches of suitable reagents, carried by zones IV, V and VI as described hereinbefore on the surface of an additional structure, involving, where appropriate the immobilisation of specifically reactive species as described hereinbefore, said additional structure together with the said sheet material providing for each of the multiplicity of devices a cavity for collecting and retaining a volume of sample liquid in contact with the said layers of suitable reagents, the cavity preferably being of capillary dimension, and (c) separating the sheet material into portions each providing one or a plurality of the sample-collecting and testing devices.

In this process, the zones of reagents contained on the second plate may be continuous if the reagents contained in the zones are of an identical nature. Alternatively, the zones of reagents contained on the second plate, like the zones of reagents contained on the first plate, may be divided into a pattern of discrete portions, for example as a two-dimensional array of patches. When such patches are formed, they can be made, for example, by firstly forming a continuous layer and then removing portions thereof to leave the desired pattern of identical reagent patches. Alternatively, the desired pattern of patches may be applied directly (for example by screen-printing), such a technique being most applicable to embodiments where, for each of the aforementioned plates, the reagents contained in the zones of said plate are not identical in nature or else are very expensive and their usage has to be kept to a minimum.

The immobilisation of a specifically reactive species onto the surface of the cavity may be carried out directly or indirectly. For example, when the specifically reactive species is an antibody, indirect immobilisation may be effected by means of an anti-species antibody which is itself bound to the said surface. Alternatively, immobilisation may be effected by conjugating an antibody with biotin and complexing with avidin pre-immobilised on the said surface; or vice versa. A further example of indirect immobilisation involves conjugating fluorescein isothiocyanate (FITC) to the specific binding partner for the species under assay and immobilising anti-FITC antibody onto said surface. Direct immobilisation may be effected by activating the said surface by treatment with a suitable reagent (e.g. a silanisation reagent such as aminopropyltrimethoxy-silane) to which the antibody can be covalently coupled using an appropriate cross-linking reagent (e.g. glutaraldehyde or glycolaldehyde). Alternative techniques well-known to the man skilled in the art may be used for immobilization of the said coating. Haptens and antigens may be immobilised directly onto the surface of the cavity by using appropriate immobilisation chemistry. Alternatively, these haptens and antigens may be conjugated to a protein e.g. poly-L-lysine and then immobilised via the protein onto the cavity surface using known methods.

For a better understanding of the present invention, reference is made to the accompanying drawings.

The following description will be made with specific reference to FCFDs possessing one auxiliary calibration surface but it will be appreciated that other devices of different design or FCFDs or other devices possessing different numbers of auxiliary calibration surfaces could be similarly constructed.

Referring to FIG. 1, the device depicted comprises an upper plate 2 fashioned of transparent material (e.g. of plastic material, quartz, silica or glass) carrying on its external face an opaque coating 8, and a lower plate 4 fashioned of transparent material, both plates being around 1 mm thick and fixed together in substantially parallel relationship, less than 1 mm apart by means of bonding tracks 38 (see FIG. 2) of suitable adhesive. In the embodiment shown, the cell cavity 6 so formed is open to the surroundings at both ends, so that when liquid sample is drawn into one opening of the cavity by means of capillarity, air may escape through the other opening. In the embodiment shown, the two plates are offset, although this is not a necessary feature.

Carried on the inner surface of the upper plate 2 are three patches of reagents appropriate to the test being carried out, being carried by zone I (12), zone II (14) and zone III (16) as defined hereinbefore. These reagents are contained within the device in a soluble releasable form (reagents X, Y and Z respectively)

Carried on the inner surface of the lower plate 4 are three patches of reagent appropriate to the test being carried out, being carried by zone IV (9), zone V (10) and zone VI (11) as defined hereinbefore, said zones 9, 10 and 11 being directly below the zones 12, 14 and 16 respectively on the plate 2. In the case of an immunoassay, the zones 9, 10 and 11 will each carry, for example, a relevant immobilised antibody or antigen or hapten. These are reagents A, B and C.

The operation in use of several embodiments of the device shown in FIG. 1 will now be described. Although the following descriptions relate to the use of a device in a labelled-antigen format competition-type immunoassay, it should be understood that devices according to the invention are also suitable for use in labelled-antibody format immunoassays (both competition-type and sandwich-type) and in other types of assay (direct, sandwich-type or competition-type) or in other types of chemical or biochemical tests.

The sample liquid passes into the device in the direction of the arrow shown in FIG. 1. A short time after the cavity 6 fills with sample liquid, the patches 12, 14, 16 or material dissolve, releasing the respective reagents into the liquid.

The success of the method of assay of the present invention depends on the spatial separation (i.e. non-mixing) of the reagents released into the sample solution form the patches 12, 14, 16. As mentioned hereinbefore, the patches 12, 14, 16 may be carried on the upper plate 2 by means of suitable dissoluble material(s). Suitable dissoluble materials include humectant coatings, e.g. sucrose- or sorbitol-based. In the embodiment shown in FIG. 1, the patches 12, 14, 16 are separated from each other. The length of the plates 2, 4 is about 15 mm, the smallest dimension of the cavity 6 is less than 1 mm (typically about 0.1 mm) and the lateral separations 18, 20 between the patches are typically 2–3 mm. The arrangement of the device is such that when filled with sample liquid, lateral mixing of reagents is very slow (typically 2 or 3 hours), whereas vertical mixing across the narrow capillary gap is rapid (several seconds only). Thus, mixing of reagents from the three patches is not a problem subsequent to the device being filled, since most tests (including immunoassays) reach equilibrium in less than 2 hours. The possibility of lateral mixing occurring is greatest during the filling of the device, when "washdown" of reagents may occur in the direction of flow of the sample liquid into the device. A further optional precaution against such washdown occurring is to coat the patches 12, 14, 16 with a thin layer of a material which provides some delayed release of the reagents within the patches. Suitable materials for coating the patches include, for example, polyvinyl alcohol (PVA). A suitable PVA coating would take typically 2–10 seconds to dissolve after initial contact of a sample liquid. In an alternative embodiment to that shown in FIG. 1, the patches 12, 14 and 16, and thereby the corresponding patches 9, 10 and 11, may be abutted. There will, in this case, be lateral mixing at the interface of the reagent patches. However, the portion of each of the zones which is subsequently selected for the purpose of measurement, as described hereinafter, is chosen so that no mixing will occur between the said portions of adjacent zones.

In one embodiment of the device of the type shown in FIG. 1 which is set up for a competition-type immunoassay for an antigen (which embodiment corresponds to the first competition-assay embodiment of the device hereinbefore described), patch 12 may contain a fluorescently labelled antigen analogue together with an amount of a specific antibody to the antigen under assay. Patch 9 would then comprise an immobilised specific binding partner being a specific antibody to the specific antibody to the antigen under assay. Thus, upon introduction of the sample liquid, the patch 12 dissolves, releasing antigen analogue and specific antibody to the antigen under assay into the sample liquid. These reagents released from patch 12 should preferably remain substantially within the region indicated in FIG. 1 by the label "T". In general, this will be the case then lateral diffusion is slow. Antigen introduced in the sample liquid competes with antigen analogue for epitopic binding sites on the specific antibody to the antigen which, either before or after such competition occurs, becomes bound to the epitopic binding sites on the layer of specific antibody contained in patch 9. The amount of fluorescent material which becomes indirectly bound to the immobilised specific antibody in patch 9 will therefore be a function of the concentration of antigen in the sample liquid. Conventional competition-type optical immunoassays involve this type of competitive equilibrium. Thus region T acts as the "measurement region". When patch 14 dissolves, a known quantity of fluorescently labelled antigen analogue in a fully saturated complex with its specific antibody is released into the sample liquid which is present in the region R as shown in FIG. 1. Thus, by comparison with region T, the antigen analogue:specific antibody complex becomes bound to the immobilised specific antibody contained in patch 10 (which will be identical to that in patch 9). Thus, initially, a maximum amount of fluorescent material is indirectly bound to the immobilised antibody in patch 10. Thus, the calibration region R acts as a "high signal calibration region". After a significant time period e.g. 1 to 2 hours, the antigen analogue bound to the immobilised antibody will compete with the antigen from the sample liquid. This competition will result in a slow decrease in the amount of fluorescent material indirectly bound to the immobilised antibody in patch 11, until the competition has reached equilibrium. When patch 16 dissolves, a known quantity of the antigen under assay in a fully saturated complex with its specific antibody is released into the sample liquid present in region S as shown in FIG. 1. Thus, in an analogus manner to region R, the antigen:specific antibody complex becomes bound to the immobilised specific antibody contained in patch 11 (which will be identical to that in patches 9 and 10). Thus, initially and subsequently, no fluorescent material becomes indirectly bound to the immobilised antibody in patch 11. Thus the calibration region S acts as a "zero signal calibration region".

For this first embodiment, the three regions T, R and S and the reagents contained therein are illustrated diagrammatically in FIG. 3a.

The subsequent descriptions of examples of the device according to the present invention are set out in terms of the three regions T, R and S as defined above. One may use any of the regions T described herein together with one of the regions R described herein (in which if a binding reaction occurs at the surface 4 in this region R it is analogous to that which occurs at the surface 4 in the region T) and optionally one or more further regions selected from any of regions R and S described herein.

In a second example of the device for a competition-type assay, the specific antibody to the antigen under assay may be contained within patch 9. In a third example, the specific antibody to the antigen under assay may be prebound to the immobilised antibody contained in patch 9. In a fourth example, the specific antibody to the antigen under assay may itself be immobilised on the surface containing patch 9. In each of these three examples, the resulting competition will be analogous to that in the measurement region described above, and in these examples are thereby described further measurement regions.

The region T for these three examples are illustrated diagrammatically in FIGS. 3b, 3c and 3d respectively.

In a fifth example the device for a competition-type assay, when patch 14 dissolves, a known quantity of fluorescently-labelled antigen analogue together with a known quantity of the antigen under assay are released into the sample liquid which is present in region R as shown in FIG. 1. In general, the quantities of antigen analogue in patches 12 and 14 will be the same, although this is not a necessary condition for successful operation of the device. Thus, by comparison with region T, antigen analogue competes with an augmented amount of antigen, for example sample antigen and antigen already in the device, for binding sites on the specific antibody which is contained in patch 10. This specific antibody is a specific antibody to the antigen under assay and is present in a saturated complex with an immobilised specific antibody contained in patch 10. The amount of fluorescent material which becomes indirectly bound to the immobilised specific antibody in patch 10 will therefore be a function of the concentration of the total amount of antigen in the region R of the sample liquid. Thus calibration region R acts as a "positive calibration region". In a sixth example, the specific antibody to the antigen under assay may itself be immobilised onto the region 10. This example results in an analogus calibration region. In a seventh example, the specific antibody to the antigen under assay may be present in a fully saturated complex with both the antigen analogue and the antigen 14, the immobilised specific antibody contained in patch 10 being a specific antibody to the specific antibody to that antigen under assay. This example results in a high signal calibration region.

The region R for these three examples is illustrated diagrammatically in FIGS. 3e, 3f and 3g respectively.

In an eighth example of the device for a competition-type assay, patch 14 may contain no reagent. The specific antibody to the antigen under assay is contained within patch 10 together with an equivalent amount of fluorescently labelled antigen analogue (the same reagent as in patch 12) and together with an equivalent amount of an immobilised specific antibody which is a specific antibody to the specific antibody to the antigen under assay. In a ninth example, the specific antibody to the antigen under assay may be prebound in a complex to the immobilised specific antibody in patch 10. In a tenth example, the antigen analogue and specific antibody to the antigen under assay may both be prebound in a complex to the immobilised specific antibody in patch 10. In an eleventh example, the specific antibody to the antigen under assay may itself be the immobilised antibody in patch 10 together with the antigen analogue preferably in a fully saturated complex. In each of these four examples, initially a maximum amount of fluorescent material becomes bound to the immobilised antibody in patch 10. Thus in these examples, region R acts as a high signal calibration region. After a significant time period e.g. 1 to 2 hours, the antigen analogue bound to the immobilised antibody will compete with the antigen from the sample liquid. This competition will result in a slow decrease in the amount of fluorescent material indirectly bound to the immobilised antibody in patch 11, until the competition has reached equilibrium.

The region R for these four examples is illustrated diagrammatically in FIGS. 3h, 3i, 3j and 3k respectively.

In a twelfth example of the device for a competition-type assay, when patch 16 dissolves fluorescently-labelled antigen analogue is released into the sample liquid present in region S as shown in FIG. 1. The specific antibody to the antigen under assay is contained within patch 11 together with an equivalent amount of the antigen under assay and together with an equivalent amount of an immobilised specific antibody which is a specific antibody to the specific antibody to the antigen under assay. In a thirteenth example, the specific antibody to the antigen under assay may be prebound in a complex to the immobilised specific antibody in patch 10. In a fourteenth example, the antigen under assay and specific antibody to the antigen under assay may both be prebound in a complex to the immobilised specific antibody in patch 10. In a fifteenth example, the specific antibody to the antigen under assay may itself be the immobilised antibody in patch 10 together with the antigen under assay preferably in a preformed complex. In each of these four examples, initially no fluorescent material will become bound to the immobilised antibody in patch 11. Thus in these four examples, region S acts as a zero signal calibration region. After a significant time period, e.g. 1 to 2 hours, the antigen bound to the immobilised antibody will become displaced by the fluorescent antigen analogue released from patch 16 resulting in a competition between the antigen and the antigen analogue. This competition process can be followed by the amount of fluorescent material that becomes bound to the immobilised specific antibody in patch 11.

The region S for these four examples is illustrated diagrammatically in FIGS. 3l, 3m, 3n and 3p respectively.

In a sixteenth and seventeenth example of the device for a competition-type assay, when patch 14 dissolves, a fluorescently labelled specific antibody, being either a specific antibody for the antigen under assay or being an antibody non-specific for the antigen under assay, is released into the sample ligand present in region R as shown in FIG. 1. The immobilised antibody which is contained within patch 10 will be a specific antibody to the fluorescently labelled antibody contained in patch 14. Thus a maximum amount of fluorescent material becomes bound to the immobilised antibody in patch 10. Thus region R acts as a high signal calibration region.

The region R for these examples are illustrated diagrammatically in FIGS. 3q and 3r respectively.

In an eighteenth example of the device suitable for a competition-type assay, no reagent is contained in patch 14. The immobilised antibody which is contained within patch 10 will be a fluorescently-labelled specific antibody either for the antigen under assay or for an antigen not being the antigen under assay. In either case, no further fluorescent material will become bound to the immobilised antibody in patch 10. The presence of the fluorescent label on the immobilised antibody will mean that region R will act as a high signal calibration region.

The region R for this embodiment is illustrated diagrammatically in FIG. 3s.

In a nineteenth example of the device suitable for a competition-type assay, when patch 16 dissolves, fluorescently labelled antigen analogue (the same reagent as in patch 12) is released into the sample liquid present in region S as shown in FIG. 1. In general, the quantity of antigen analogue in patch 16 will be the same as the quantity in patch 12, although this is not a necessary condition for successful operation of the device. The immobilised antibody which is contained within patch 11 will be a binding partner non-specific for the antigen in the sample liquid. Thus, no fluorescent material will become bound to the immobilised antibody in patch 11. Thus, region S acts as a zero signal calibration region.

The region S for this embodiment is illustrated diagrammatically in FIG. 3t.

In a twentieth example of the device for a competition-type assay, when patch 16 dissolves, a fluorescently labelled antigen analogue, the antigen being distinct from the antigen under assay, is released into the sample liquid present in region S as shown in FIG. 1. The antibody which is contained within patch 11 will be a specific binding partner for the antigen under assay. Thus, no fluorescent material will become bound to the immobilised antibody in patch 11. Thus, region S acts as a zero signal calibration region.

The region S for this embodiment is illustrated diagrammatically in FIG. 3u.

In a twenty-first example of the device for a competition-type assay, when patch 14 dissolves, fluorescently labelled antigen analogue (the same reagent as in patch 12) is released into the sample liquid present in region R as shown in FIG. 1. The antibody which is contained within patch 10 will be a binding partner non-specific for the antigen in the sample liquid together with an amount of a fluorescently labelled analogue of the antigen which is a specific binding partner for the antibody in patch 10 in a complex, which has preferably been preformed in the patch 10. Thus, a maximum amount of fluorescent material becomes bound to the immobilised antibody in patch 10. Thus, region R acts as a high signal calibration region.

The region R for this embodiment is illustrated diagrammatically in FIG. 3v.

Figures 4M, 4N, 4P, 4Q, 4R, 4S, 4T:
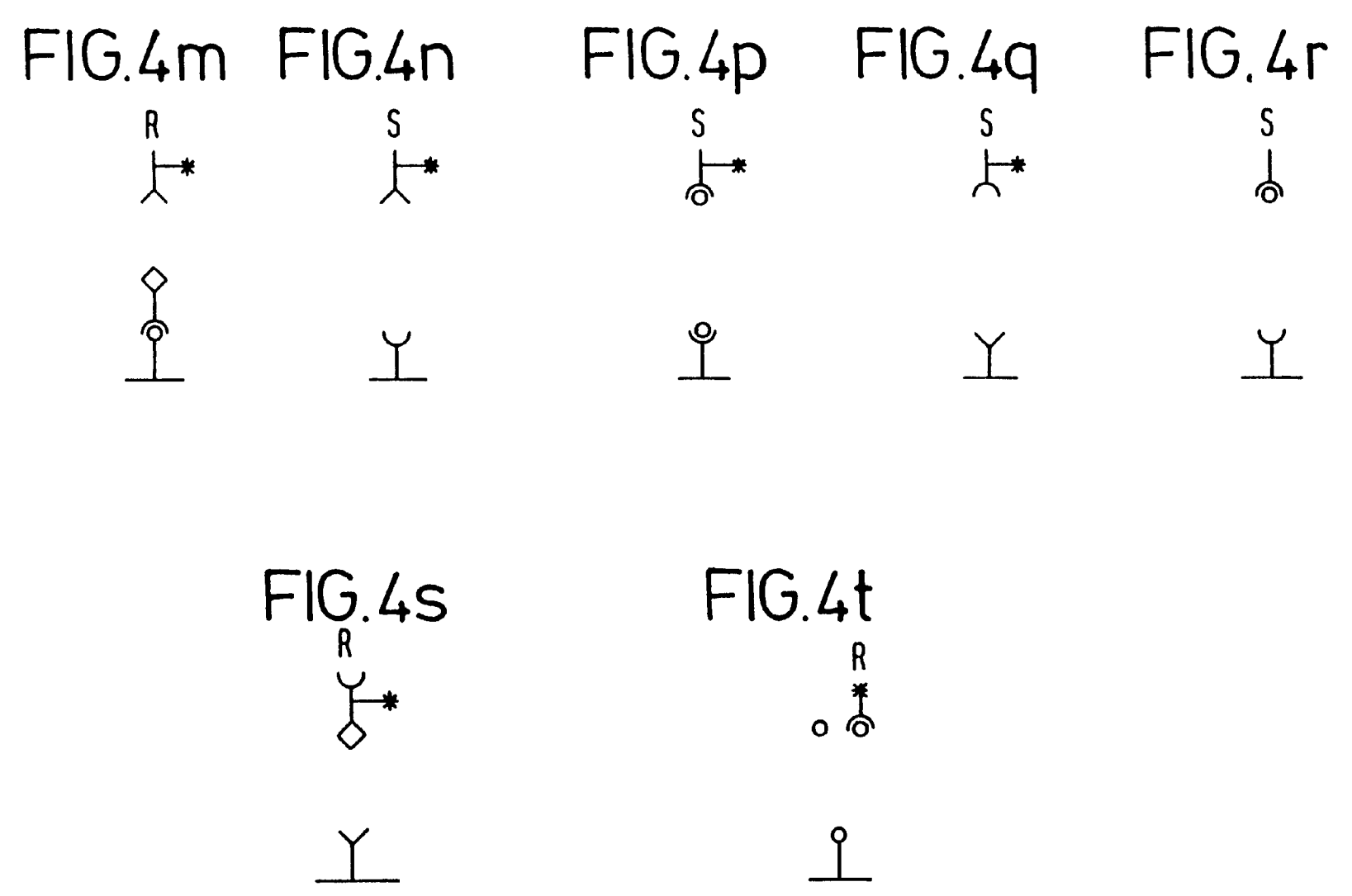

Further examples of embodiments of the device for a competition-type assay are illustrated in FIGS. 4a to 4t. FIGS. 4a to 4c illustrate examples of the measurement region T. FIGS. 4d and 4e illustrate examples of a positive calibration region R. FIGS. 4f to 4m illustrate examples of a high signal calibration region R. FIGS. 4n to 4r illustrate examples of a zero signal calibration region S. With the exception of FIGS. 4g, 4h, and 4r, these examples include the use of labelled-antibody. FIGS. 4a, 4e, 4f, 4h, 4k and 4l illustrate the use of a species such as, for example, poly-L-lysine, bovine serum albumin or keyhole limpet haemocyanin, to facilitate immobilisation of the antigen in the relevant patch. FIG. 4b illustrates an alternative use of a species such as, for example, avidin to facilitate the antigen-antibody binding reaction.

For the direct assay embodiments of the device hereinbefore described, the example of the measurement region T is illustrated in FIG. 5n. Examples of a positive calibration region R are illustrated in FIGS. 5p and 5q. Examples of a high signal calibration region R are illustrated in FIGS. 5r to 5t. The calibration region S is illustrated in FIG. 5u, being a zero signal calibration region.

Figure 5A:
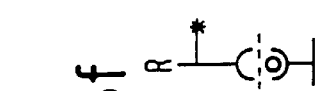
FIG. 5(a) diagrammatically illustrates a sandwich assay measurement region T.
Figure 5B:
FIG. 5(b) diagrammatically illustrates a sandwich assay positive calibration region R.
Figure 5C:
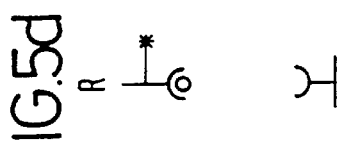
FIG. 5(c) diagrammatically illustrates high signal calibration region R of a first sandwich assay embodiment of the invention.
Figure 5D:
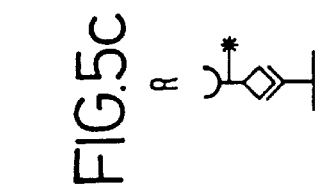
FIG. 5(d) diagrammatically illustrates high signal calibration region R of a second sandwich assay embodiment of the invention.
Figure 5E:
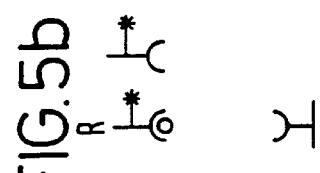
FIG. 5(e) diagrammatically illustrates high signal calibration region R of a third sandwich assay embodiment of the invention.
Figure 5F:
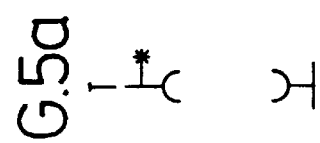
FIG. 5(f) diagrammatically illustrates high signal calibration region R of a fourth sandwich assay embodiment of the invention.
Figure 5G:
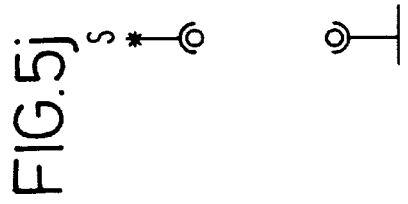
FIG. 5(g) diagrammatically illustrates high signal calibration region R of a fifth sandwich assay embodiment of the invention.
Figure 5H:
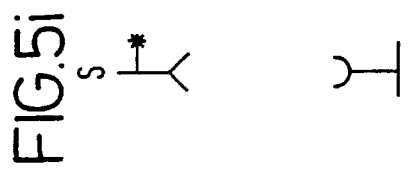
FIG. 5(h) diagrammatically illustrates high signal calibration region R of a sixth sandwich assay embodiment of the invention.
Figure 5I:
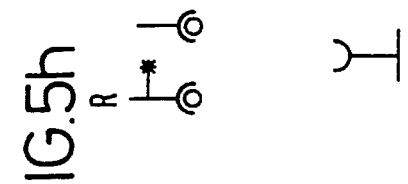
FIG. 5(i) diagrammatically illustrates zero signal calibration region S of a first embodiment of sandwich assays.
Figure 5J:
FIG. 5(j) diagrammatically illustrates zero signal calibration region S of a second embodiment of sandwich assays.

For the sandwich assay embodiments of the device hereinbefore described, an example of the measurement region T is illustrated in FIG. 5a. An example of a positive calibration region R is illustrated in FIG. 5b. Six examples of a high signal calibration region R are illustrated in FIGS. 5c to 5h. Two examples of a zero signal calibration region S are illustrated in FIGS. 5i and 5j.

Certain examples of calibration regions described for use in a competition-type assay may find use in a sandwich assay embodiment of the device and vice versa. FIGS. 5c and 5g illustrate two such examples used in both competition-type and sandwich-type assays.

In all of the examples hereinbefore described, the same fluorescent species is used as a fluorescent label on those reagents stated to be labelled.

In the embodiment of the device shown in FIG. 1, the patch 12 (being zone I as defined hereinbefore) is the closest of the three patches on plate 2 to the end of the device where introduction of the sample liquid occurs, whilst the patch 16 (being zone III) is the furthest of the three patches on plate 2 from said end of the device. In alternative embodiments of the device, the patches 12, 14 and 16 and thereby the corresponding patches 9, 10 and 11 may be arranged in any order from the end of the device where introduction of the sample liquid occurs.

In the various embodiments of the device according to the invention as defined hereinbefore, one pair of zones provides the measurement region whereas the other two pairs of zones provide calibration regions, such calibration regions being selected from a positive calibration region, a zero signal calibration region or a high-signal calibration region.

In several of the embodiments of the device as defined hereinbefore, in order to give the desired signal, consideration must be given to the kinetic characteristics of the various binding reactions involved. The reagents are chosen and the signals from the various regions read at the appropriate time to achieve the desired signal. For certain formats, it is important to ensure that the binding of the intended species occurs and no dissociation occurs in any complex initially formed prior to the reading of the signal.

Further embodiments of the device with only one calibration region or with three or more calibration regions suggest themselves and are included within the scope of the present invention, the calibration regions being preferably selected from those described hereinbefore or those described hereinafter in the Examples.

Assay measurements are obtained by illuminating in turn with light of an appropriate frequency or range of frequencies the portions of the immobilised layer (or a part only of said portion) which lies in region T, region R and region S. This light leads to excitation of fluorophores within the region of illumination. These fluorophores then fluoresce and emit light, some of which passes into the second plate 4 and is guided by said plate to emerge from the smooth edge 22 with characteristics as described in EP-A-171148, which light may then be filtered and analyzed as desired.

Sequential illumination of the different zones 9, 10 and 11 may be effected by a shuttering mechanism in the illumination optics, details of which will be apparent to one skilled in the art. The optical signals arising from fluorescent species in each zone will all emerge in turn from the optical edge 22 and be detected by the same optical detector before being processed in a desired manner. Alternatively, illumination of the different regions of the immobilised layer 10 may be effected by use of a number of identical light sources. Alternatively, it is possible to use a single light source and index the device past the light source thereby sequentially illuminating the different regions of the immobilised layer 10.

Although the preceding discussion is made with particular reference to fluorescent labels, it will be appreciated that it also applies to reagents conjugated to labels which exhibit other properties (e.g. phosphorescence or luminescence).

Figure 2:
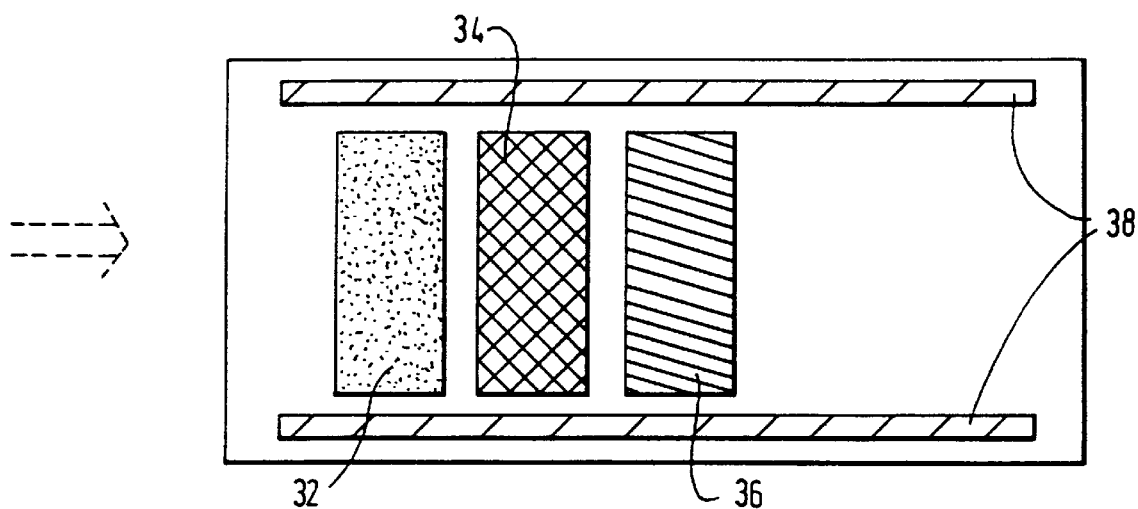
FIG. 2 is a planned view of the device of FIG. 1.

FIG. 2 shows a plan view of the lower plate of the device shown in FIG. 1. The patches of material 32, 34, 36 correspond to those labelled 12, 14, 16 respectively in FIG. 1. Also shown in FIG. 2 are the bonding tracks 38 which cause mutual adhesion of the upper and lower plates of the device. The depth of the capillary gap may be defined by incorporating glass ballotini of appropriate diameter (for example, about 100 microns) in the glue which is used for the bonding tracks 38.

The method of the invention is particularly applicable to assays of antigens or antibodies, i.e. to immunoassays, and in a preferred embodiment of the invention the ligand is an antigen and the specific binding partner comprises an antibody to the said antigen. However, the invention is not to be taken as limited to assays of antibodies or antigens. Examples of ligands which may be assayed by the method of the invention are given in Table 1 below together with an indication of a suitable specific binding partner in each instance.

TABLE

| Ligand | Specific Binding Partner |
| --- | --- |
| antigen | specific antibody |
| antibody | antigen |
| hormone | hormone receptor |
| hormone receptor | hormone |
| polynucleotide strand | complementary polynucleotide strand |
| avidin | biotin |
| biotin | avidin |
| protein A | immunoglobulin |
| immunoglobulin | protein A |
| enzyme | enzyme cofactor (substrate) or inhibitor |
| enzyme cofactor (substrate) or inhibitor | enzyme |
| lectins | specific carbohydrate |
| specific carbohydrate of lectins | lectins |

The method of the invention has very broad applicability but in particular may be used to assay: hormones, including peptide hormones (e.g. thyroid stimulating hormone (TSH), luteinizing hormone (LH), human chorionic gonadotrophin (hCG), follicle stimulating hormone (FSH), insulin and prolactin) or non-peptide hormones (e.g. steroid hormones such as cortisol, estradiol, progesterone and testosterone, or thyroid hormones such as thyroxine (T4) and triiodothyronine), proteins (e.g. carcinoembryonic antigen (CEA) and antibodies and alphafetoprotein (AFP)), drugs (e.g. digoxin, drugs of abuse), sugars, toxins, vitamins, viruses such as influenza, para-influenza, adeno-, hepatitis, respiratory and AIDS viruses, virus-like particles or microorganisms.

It will be understood that the term "antibody" used herein includes within its scope:

(a) any of the various classes or sub-classes of immunoglobulin, e.g. IgG, IgA, IgM, or IgE derived from any of the animals conventionally used, e.g. sheep, rabbits, goats or mice, (b) monoclonal antibodies, (c) intact molecules or "fragments" or antibodies, monoclonal or polyclonal, the fragments being those which contain the binding region of the antibody, i.e. fragments devoid of the Fc portion (e.g. Fab, Fab', F(ab')$_2$), the so-called "half-molecule" fragments obtained by reductive cleavage of the disulphide bonds connecting the heavy chain components in the intact antibody or fragments obtained by synthetic methods.

The method of preparation of fragments of antibodies is well known in the art and will not be described herein.

The term "antigen" as used herein will be understood to include both permanently antigenic species (for example, proteins, bacteria, bacterial fragments, cells, cell fragments and viruses) and haptens which may be rendered antigenic under suitable conditions.

Examples of fluorophores which may be used in the method of assay according to the invention include fluorescein and its derivatives (e.g. fluorescein isothiocyanate (FITC)), rhodamine and its derivatives (e.g. XRITC, TRAP, TRITC), lucifer yellow, 2,4-dinitrofluoro-benzene, phenylisothiocyanate, dansyl chloride, phycobiliproteins (e.g. allophycocyanin and phycoerythrin) and indocyanins.

The present invention further provides apparatus suitable for use in the method of assay according to the invention as hereinbefore described which comprises a fluorescence capillary fill device according to the invention as hereinbefore defined; a source of radiation capable of being arranged such that, in use, radiation enters the said device such that fluorophores are excited; and means for monitoring the emerging radiation. In a further embodiment, the device can be illuminated via a mask, thereby defining the effective volume of the device in which the binding reaction occurs. The effective volume is the product of the distance between base and top plates of the device and the area of the illumination zone as defined by the mask 55 in the optical train.

The present invention further provides a kit for performing a method of assay according to the present invention comprising a device as hereinbefore defined together with appropriate ancillary reagents.

In a quantitative competition assay, it is necessary to have an accurate measurement of the concentration of a particular analyte in a sample. Various factors may alter the level of the observed signal in the assay and it is therefore essential to have a sufficient number of defined signals relating to particular concentrations of analyte to enable a standard assay curve to be constructed. Thus, by using a variety of calibration regions wherein the initial binding of fluorophore to the calibration surface can be pre-determined by suing a known amount of reagents as described in the embodiments hereinbefore, such defined signals can be achieved which will also compensate for the various factors outlined above. In general, known assay techniques employ a 4 or 5 point calibration procedure and so for a quantitative assay, it is preferable to have more than three calibration regions and most preferably five or greater.

In a qualitative or semi-qualitative competition assay, it is only necessary to determine whether a sample has more or less than a certain concentration of a particular analyte, this concentration being called the 'cutoff level' for the particular assay. Therefore, by relating the measured amount of the analyte in a sample to this 'cutoff level', one can determine whether the sample is 'positive' or 'negative'. Such a 'cutoff level' is generally chosen as the point referring to a 50% level of binding to the measurement surface of the species giving rise to the signal although other points may be chosen as the cut-off level.

Similar considerations apply to sandwich assays. In such assays, however, due to the fact that the amount of fluorophore binding to the measurement surface is directly proportional to the amount of sample analyte, a straight-line standard assay graph needs to be constructed. This is easier to achieve than the construction of a standard assay cure for a competition assay. In general, therefore, a quantitative assay requires only a 3-point calibration procedure; therefore it is preferable to have 2 calibration regions, more preferably 3 in a sandwich-type assay.

In the various embodiments described hereinbefore for either a competition or sandwich assay, the "high signal calibration regions" have been particularly designed so that an initial maximum amount of fluorescent material becomes bound to the surface. However, by altering the amounts of the various reagents concerned, different amounts of fluorescent material may initially become bound resulting in other non-zero signals arising from these regions, such amounts being chosen to given signals corresponding to the 'cutoff level' required. Examples include those illustrated in FIGS. 3g, 3w, 3s, 3v, 3h, 3i, 3j, 3k, 3x, 4g, 4h, 4k, 4l, 4t, 5c, 5e, 5f, 5g and 5h.

The "positive calibration regions" as previously described for a competition-type assay are preferably designed so that the signal relates to a 'cutoff value' corresponding to the inflection point of the standard assay curve.

The zero signal calibration regions as previously described give a signal corresponding to the background signal for the assay device. For a competition assay, the regions are designed such that the signal obtained corresponds to the low asymptote of the standard assay curve, whereas for a sandwich assay, the regions are designed such that the signal corresponds to the lower limit of the standard assay graph.

The following Examples serve to illustrate embodiments of the present invention without, however, limiting it.

Examples 1 to 8 illustrate embodiments of the invention in which an antigen-labelled format for a competitive assay of an antigen is described.

EXAMPLE 1

1. Preparation of Starting Materials

1.1 Fabrication of Antibody-coated Waveguides

A sheet of Permabloc class (Pilkington Glass Ltd., St. Helens, UK) having a thickness of about 1 mm was cleaned with detergent (e.g. TWEEN (trademark) 20) in ultra-pure water with ultrasonic agitation. The surface of the glass was activated by incubating it in a 2% solution of aminopropyltriethoxysilane in water at a pH of 3 to 4 for two hours at 75° C. After rinsing in water, the glass sheet was dried at 115° C. for at least four hours. The glass was then incubated for 60 minutes in a 2.5% solution of glutaraldehyde in a 0.05M phosphate buffer (pH 7), and then washed thoroughly with distilled water. The glass was incubated for two to four hours in a 1 percent solution of a rat anti-mouse monoclonal antibody in phosphate buffer (pH 7). The glass sheet was then washed with buffer solution. Unwanted adsorbed protein was removed by soaking with a 6M urea solution in known manner. This formed plate 4 of the FCFD test device as illustrated in FIG. 1.

1.2 Preparation of Morphine Conjugated to Fluorescein Isothiocyanate (FITC)

200 mg of FITC (Sigma Chemical Company Ltd., UK) and 5 mg of morphine-3-glucuronide were mixed together in 1.4 ml of 0.2 M sodium bicarbonate buffer solution (pH 9.0). The mixture was left for 18 hours at room temperature, during which conjugation of FITC to the morphine occurred. The mixture was then purified by gel filtration on SEPHADEX G-50 superfine.

1.3 Microdosing of the Specific Reagents Over Each Discrete Reference Zone

An opaque coating was screen printed onto a clean sheet of Permabloc glass as described in WO-90/14590. The measurement zone (zone I) was fabricated by microdosing a layer of morphine-FITC conjugate followed by a separate layer of mouse anti-morphine monoclonal antibody in an area 3×7 mm onto the glass over zone I. Each layer was allowed to air dry before a second reagent layer was added on top of it. Since the layers are fabricated in discrete stages, there is no preferential binding of the morphine FITC to the anti-morphine monoclonal antibody when the patient sample is introduced at the time of assay.

In this Example, zone II was fabricated to produce a signal equivalent to the high asymptote of the standard curve from the measurement zone by using a premix of the mouse anti-morphine monoclonal antibody and morphine-FITC conjugate accurately microdosed over the zone II area.

Zone III was fabricated to produce a signal equivalent to the low asymptote of the assay as defined by the measurement standard curve by using a premix of mouse anti-morphine monoclonal antibody and morphine accurately microdosed over the zone III area.

This glass sheet containing zones I, II and III forms the plate 3 of the FCGD test device as illustrated in FIG. 1.

1.4 Fabrication of FCFD Test Devices

Test devices such as have been described in EP-A-0171148 were fabricated by screen printing onto the waveguide resulting from step 1.1 above bonding tracks of an ultraviolet curing glue (UVS 91, Norland Inc., USA) containing glass microspheres of diameter 100 microns (Jencons Ltd., UK) in a pattern defining the long edges of the capillary cell devices (see FIG. 2). A sheet of glass as defined in 1.3 above was then placed over the waveguide, and a vacuum applied to the laminate. As result of the vacuum, the upper sheet of glass was caused to press down onto the glue, the glass microspheres defining a gap of 100 microns between the glass sheets. The laminate was then exposed to an ultraviolet light source to cure the glue. Finally, the laminate sheet was broken into individual test devices as described in EP-A-0171148.

1.5 Preparation of Morphine Standard Solutions

A freeze-dried preparation of morphine-3-glucuronide was obtained from Sigma Chemical Company Ltd. This sample was diluted in pooled human urine buffered to pH 7.5, to give the range of morphine standards required.

1.6 Apparatus Used in the Measurement of the Morphine Assay

Figure 6:
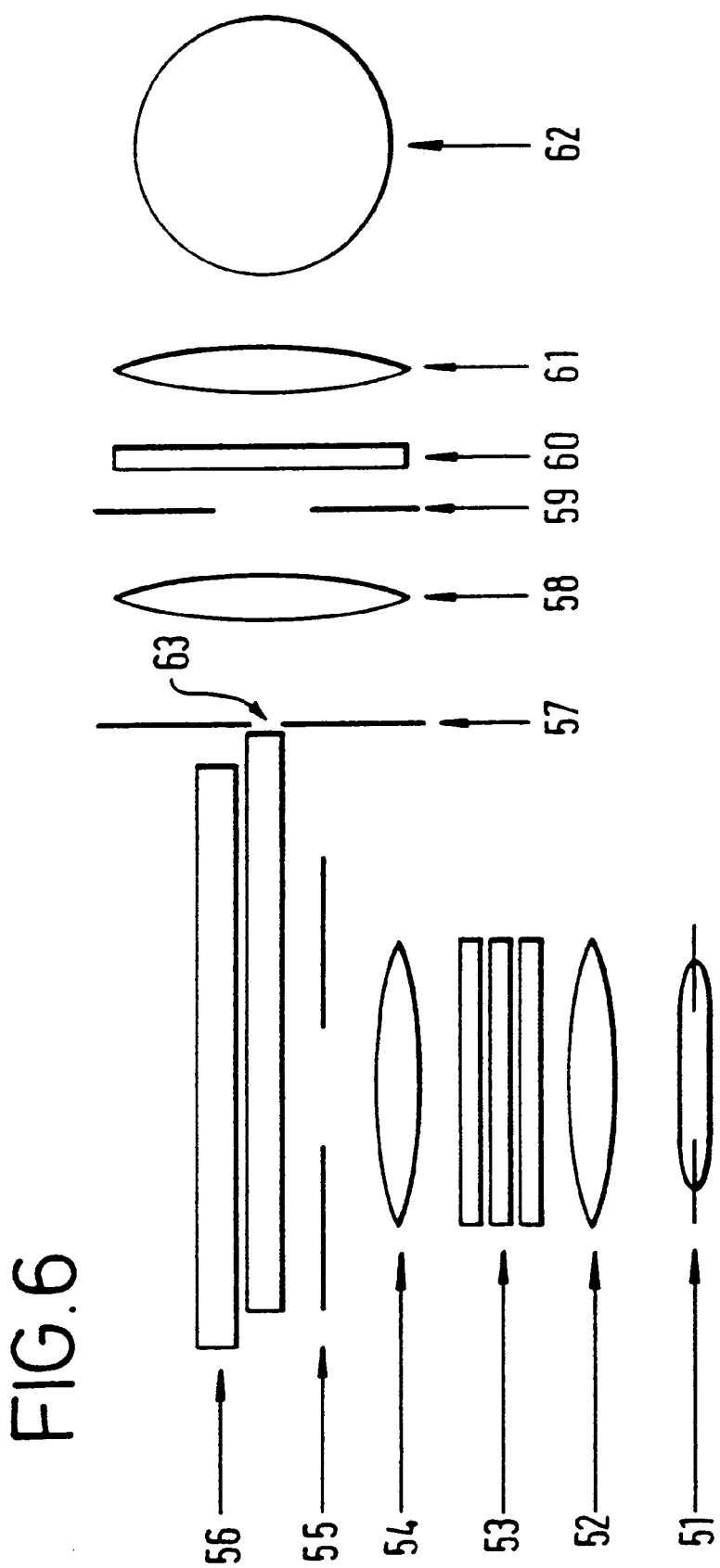
FIG. 6 shows schematically a simple fluorimetry apparatus.

FIG. 6 shows a simple fluorimetry apparatus which was used to make suitable assay measurements as described in GB8911462.3. Light from a zenon flash lamp 51 (Heinmann) is roughly collimated by a lens 52 before passing through a filter stack 53 which defines the wavelength range used to excite the FITC-labelled antibodies. The filter stack comprises three filters: a BG7 Schott glass filter (Ealing Electro Optics UK Ltd., Watford, UK) a 450–480 nm FITC bandpass interference filter (Optometrics Ltd., UK) and a 474 nm shortpass interference filter (Comar Instruments Ltd., Cambridge, UK). A second lens 54 focused the excitation light onto the active surface of the test cell 56 through an aperture 55 which defines the illuminated area and hence the active volume of the test cell.

Light emitted from the optical edge 63 of the test cell passes through an aperture 57 which prevents light emitted directly out of the solution from entering the detection optics.

A lens system 58 collects the emitted light and an aperture 59 defines the angular range over which the emission is measured. This was chosen to coincide with angles associated with evanescently coupled fluorescence emission. A Schott CG515 515 nm colloidal glass longpass filter 60 (Ealing Electro Optics UK Ltd., Watford, UK) filters out any scattered pump light and a second lens 61 focuses the emission onto a photomultiplier detector 62 (Hamamatsu P931A, Hakuto UK Ltd).

3. ASSAY PROCEDURE FOR MORPHINE

Figure 7:
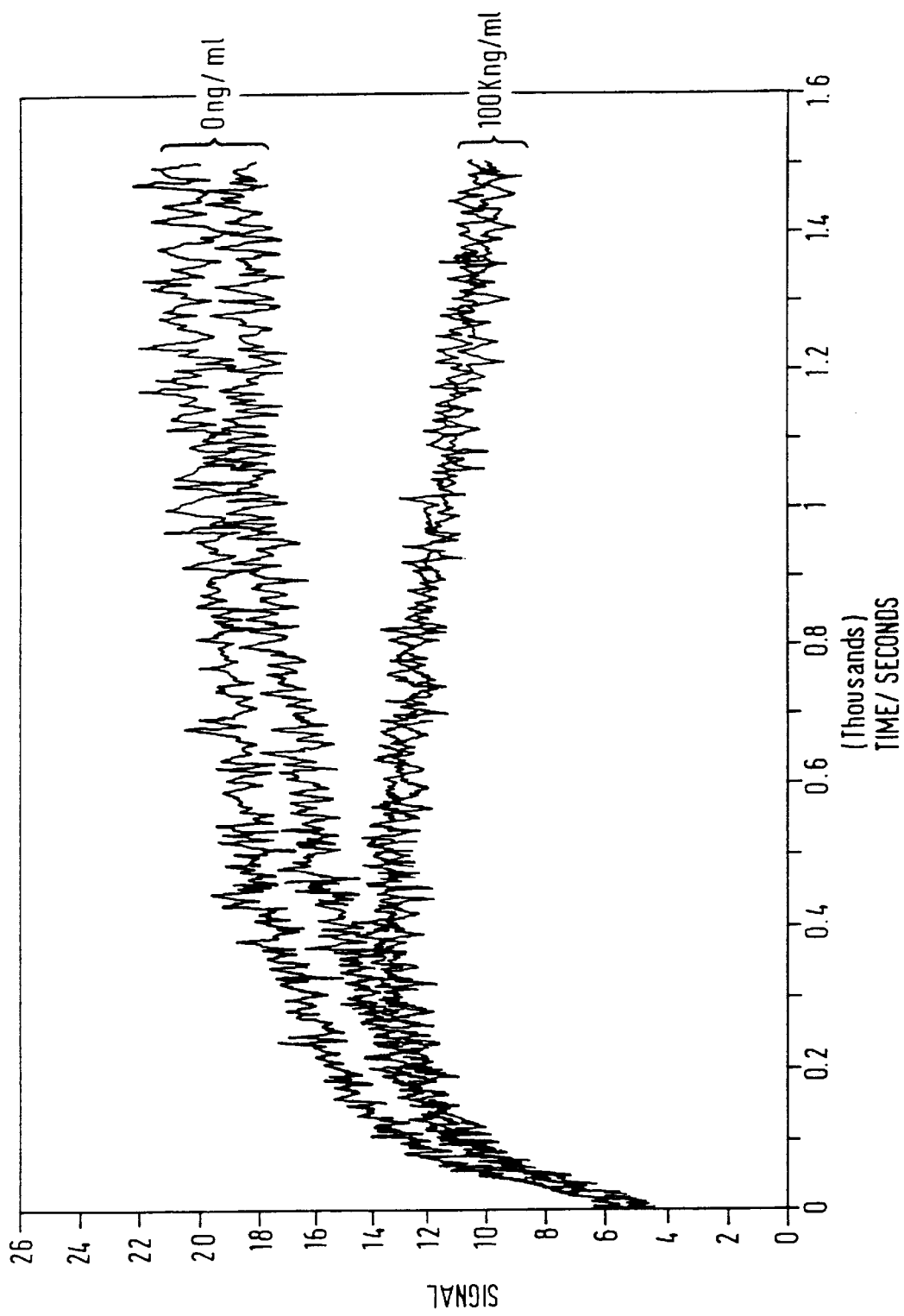
FIG. 7 is a plot of signal versus time in zone V of example 1.
Figure 8:
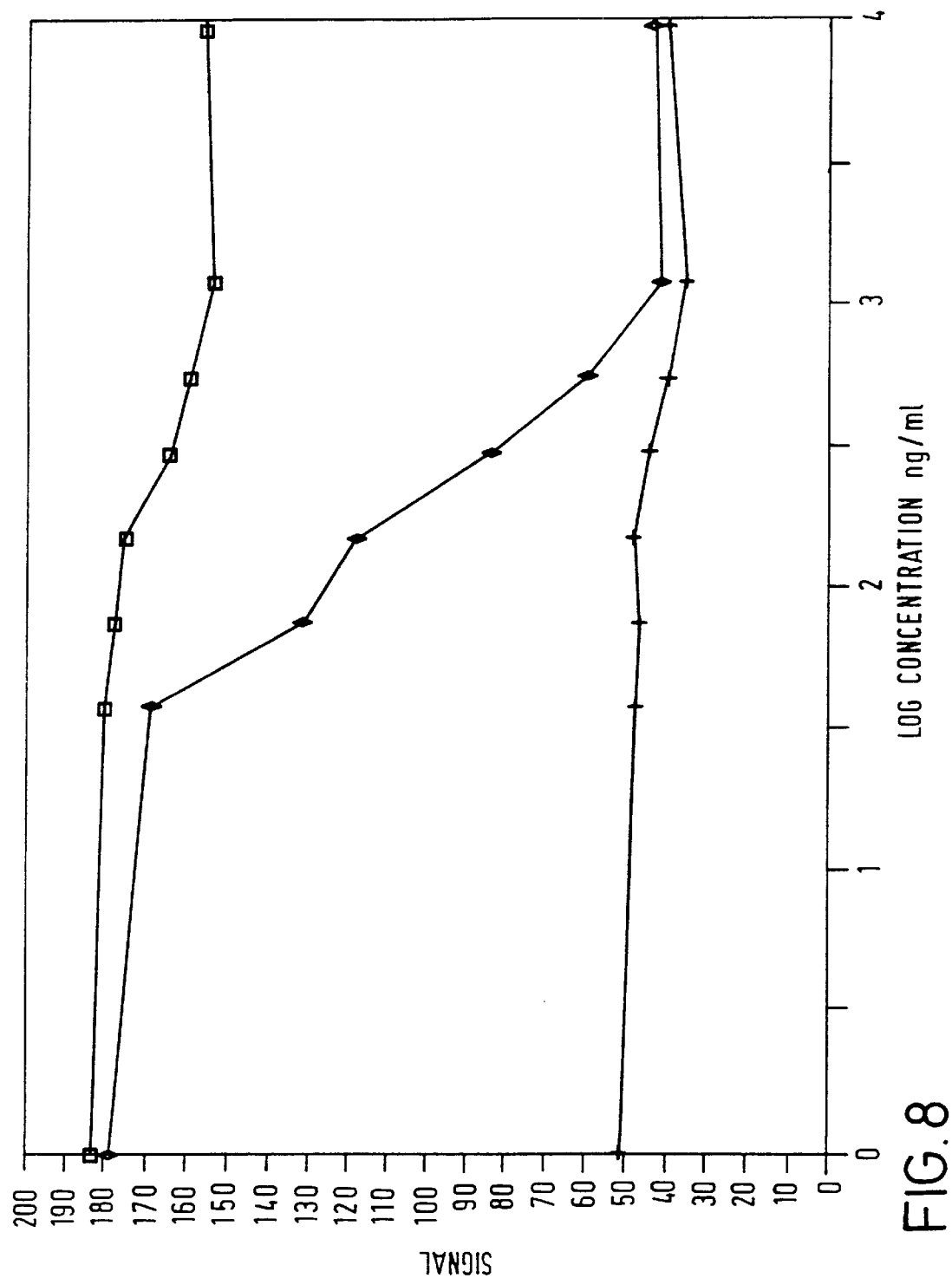
FIG. 8 is a plot of signal versus log concentration in zone IV of example 1.

Eight test CFDs were chosen to produce a standard curve and each was filled with a different morphine standard solution. The CFDs were read after an incubation in a humid environment. Zones V and VI were read after 3 minutes of incubation, so that the measured signal could be considered to represent the high and low asymptote respectively for the assay—(ie, before significant dissociation had occurred). FIG. 7 shows a plot of signal versus time for zone V. It is apparent from this that between 0 and 200 seconds the signal is independent of the analyte concentration, whereas after 200 seconds the labelled reagent begins to dissociate from the base plate and competition between the labelled ligand analogue and the ligand occurs so that the signal becomes dependent upon the analyte concentration. Hence this zone (and also zone VI) must be read before 200 seconds have elapsed. Zone IV was read after a 15 minute incubation (after the assay had reached equilibrium). From this zone, the standard curve was generated (FIG. 8). [It will be appreciated that the time before which the reference zone must be read (200 seconds in this particular example) will be dependent on the particular assay system and reagents used]. FIG. 8 shows that the signal from zone IV can be used to derive the analyte concentration in the patient sample. Zones V and VI produce a signal which can be used to fix the assay high and low asymptote respectively. At the read time chosen, the signals produced from zones V and VI are independent of analyte concentration.

Thus the signal from zone IV can be compensated for any change in background fluorescence or assay range by using the measured values from zones V and VI, and comparing them to reference data for zones V and VI obtained during device fabrication.

EXAMPLE 2

1. PREPARATION OF STARTING MATERIALS 1.1 Fabrication of Antibody-coated Waveguides As for example 1, with the exception that zones V and IV were treated with a premixed solution of rat anti-mouse and mouse anti-morphine antibodies. Zone VI was not used in this example.

1.2 Preparation of Morphine Conjugated to Fluorescein Isothiocyanate (FITC)

As for example 1.

1.3 Microdosing of the Specific Reagents Over Each Discrete Reference Zone

As for example 1, except that zone II has a layer of morphine FITC conjugate and unlabelled morphine (either as a premixed solution or as separate layers) microdosed on to the glass. Zone III is microdosed with morphine FITC conjugate.

1.4 Fabrication of FCFD Test Devices

As for example 1.

1.5 Preparation of Morphine Standard Solutions

As for example 1.

1.6 Apparatus Used in the Measurement of the Morphine Assay

As for example 1.

3. ASSAY PROCEDURE FOR MORPHINE

The CFDs were filled with a range of morphine standards and read after an incubation in a humid environment.

Figure 9:
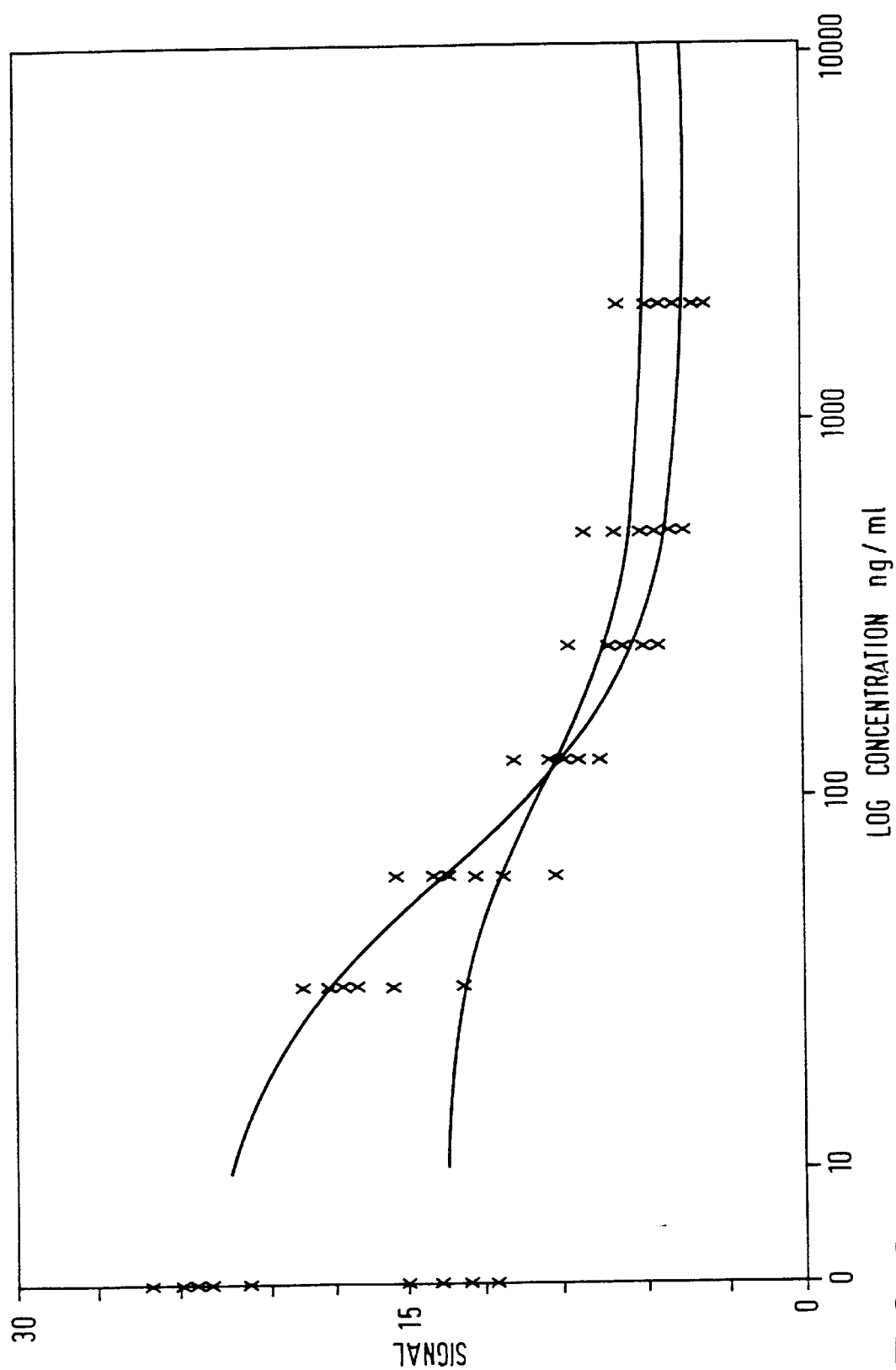
FIG. 9 is a plot of signal versus log concentration of zones IV and V in example 2.

Zones IV and V were read when the assay had come to equilibrium—i.e. fifteen minutes. (FIG. 9). Zone IV is the assay measurement zone. Zone V shows an offset when compared to zone IV at low analyte concentrations. This zone is used to define the assay cutoff. Thus when zone IV is x units larger then zone V, the patient sample is considered to be negative in a competition assay. Furthermore, when the sample from zone IV is y units less than zone V, the patient sample is considered to be positive. It is anticipated that zones VI and III would be used to complete the calibration regions, by treating the plate carrying zone VI with rat anti-mouse antibody and the plate carrying zone III with a combined complex of mouse anti-morphine antibody with morphine FITC conjugate.

Zone VI would be read after 3 minutes of incubation so that the measured signal could be considered to represent the high asymptote of the assay and is independent of the morphine concentration of the patient sample. Thus zone V would be used to define the cutoff position and zone VI to confirm that the reagents were working, regardless of patient sample concentration.

EXAMPLE 3

1. PREPARATION OF STARTING MATERIALS 1.1 Fabrication of Antibody-coated waveguides.

As for example 1, except that zones IV and V were treated with a premixed solution of rat anti-mouse and mouse anti-morphine antibodies. Zone VI was not used in this example.

1.2 Preparation of morphine conjugated to fluorescein isothiocyanate (FITC).

As for example 1.

1.3 Microdosing of the Specific Reagents Over Each Discrete Reference Zone

As for example 1 except that zone II has a layer of morphine-FITC conjugate and unlabelled morphine (either as a premixed solution or as separate layers) microdosed onto the glass and zone I is microdosed with morphine FITC conjugate. Zone III is not used in this Example.

1.4 Fabrication of FCFD Test Devices

As for example 1.

1.5 Preparation of Morphine Standard Solutions

As for example 1.

1.6 Preparation of Morphine Standard Solutions Using Adulterated Urine:

Urine sample were obtained from volunteers known not to be taking morphine and, after pooling, the samples were treated as follows:

a) The pH of the urine increased to pH 10 by the addition of sodium hydroxide.

b) The pH of the urine decreased to pH 4.5 by the addition of hydrochloric acid.

c) The pH of the urine decreased to pH 4.0 by the addition of hydrochloric acid.

d) The fluorescence of the urine increased by the addition of TRAP to give a final concentration of 1 um/L.

e) The fluorescence of the urine increased by the addition of TRAP to give a final concentration of 6 um/L.

Morphine standard solutions were then made up using these 5 types of urine as in example 1, giving a range of morphine concentrations above and below the assay cut-off.

1.7 Apparatus used in the measurement of the morphine assay

As for example 1.

3. ASSAY PROCEDURE FOR MORPHINE

Assay curves were generated using eight standards in triplicate using unadulterated urine. Samples made of from the adulterated urines were assayed and their the signals obtained from the values read off the standard curve. The signals obtained from the measurement and reference zones were used for each type of sample using the procedure described in example 2.

Figure 10A:
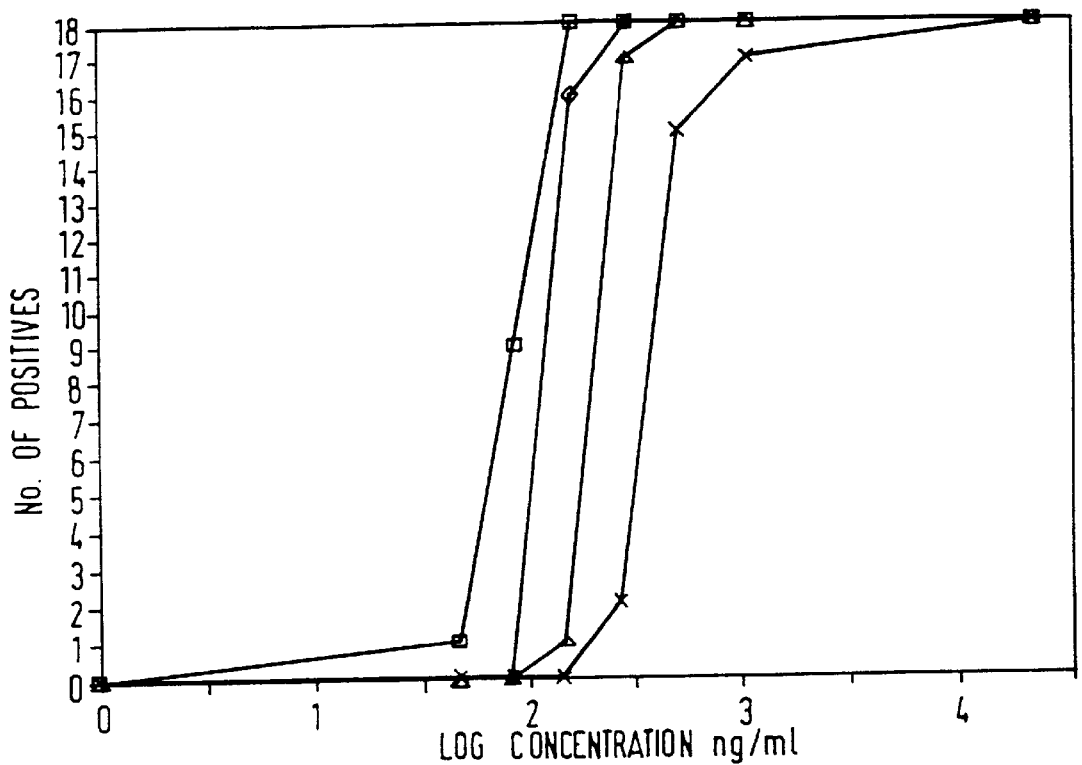
FIGS. 10(a) and 10(b) are plots of positive results versus log concentration in example 3.
Figure 10B:
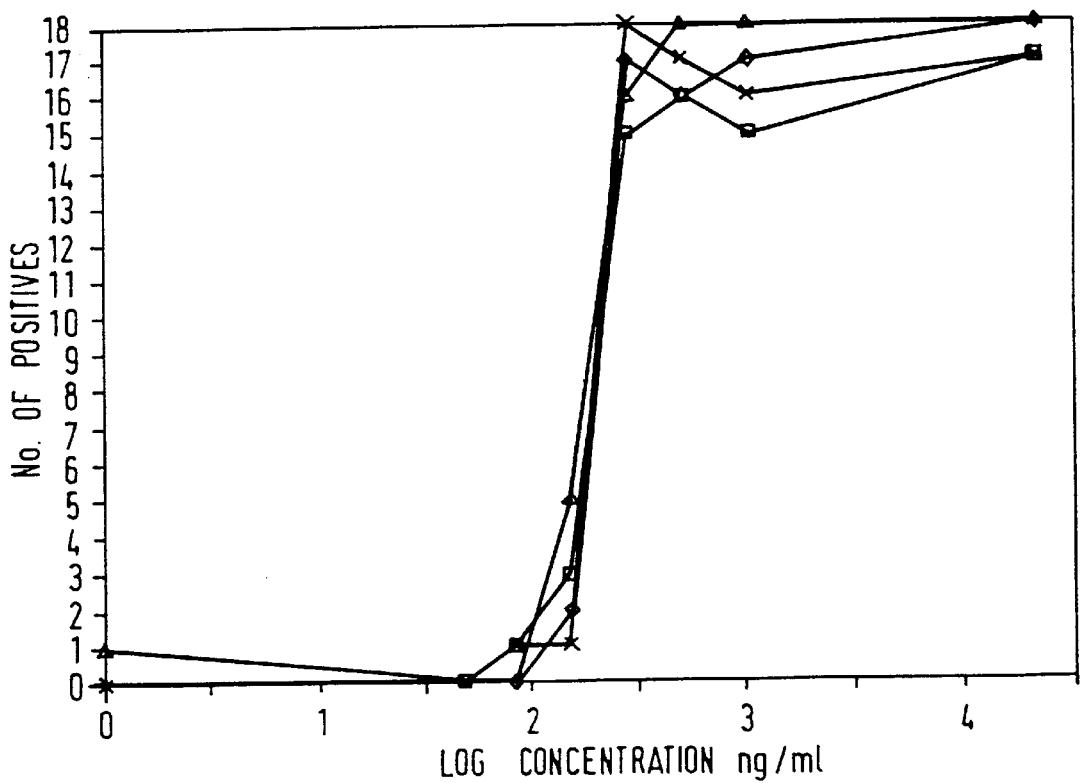

FIGS. 10a and 10b show plots of the number of positive results against dose for various urine types using firstly the standard assay method (FIG. 10a) and then the positive control reference format (10b). Ideally the step change between positive and negative samples should be abrupt but with the standard assay method, this step change varies with sample type. Use of the reference zone results in the curves being much more tightly grouped.

EXAMPLE 4
1. PREPARATION OF STARTING MATERIALS 1.1 Fabrication of Antibody-coated Waveguides As for example 1, with the exception that zone V was treated with a mouse monoclonal antibody (against hCG) labelled with FITC and zone IV was treated with a premix of rat antimouse antibody and mouse anti morphine antibody.

1.2 Preparation of Morphine Conjugated to Fluorescein Isothiocyanate (FITC)

As for example 1.

1.3 Microdosing of the Specific Reagents Over Each Discrete Reference Zone

As for Example 1 except that the morphine-FITC conjugate was microdosed onto zone I only.

1.4 Fabrication of FCD Test Devices

As for example 1.

1.5 preparation of Morphine Standard Solutions

As for example 1.

1.6 Apparatus Used in the Measurement of the Morphine Assay

As for example 1.

3. ASSAY PROCEDURE FOR MORPHINE

Figure 11:
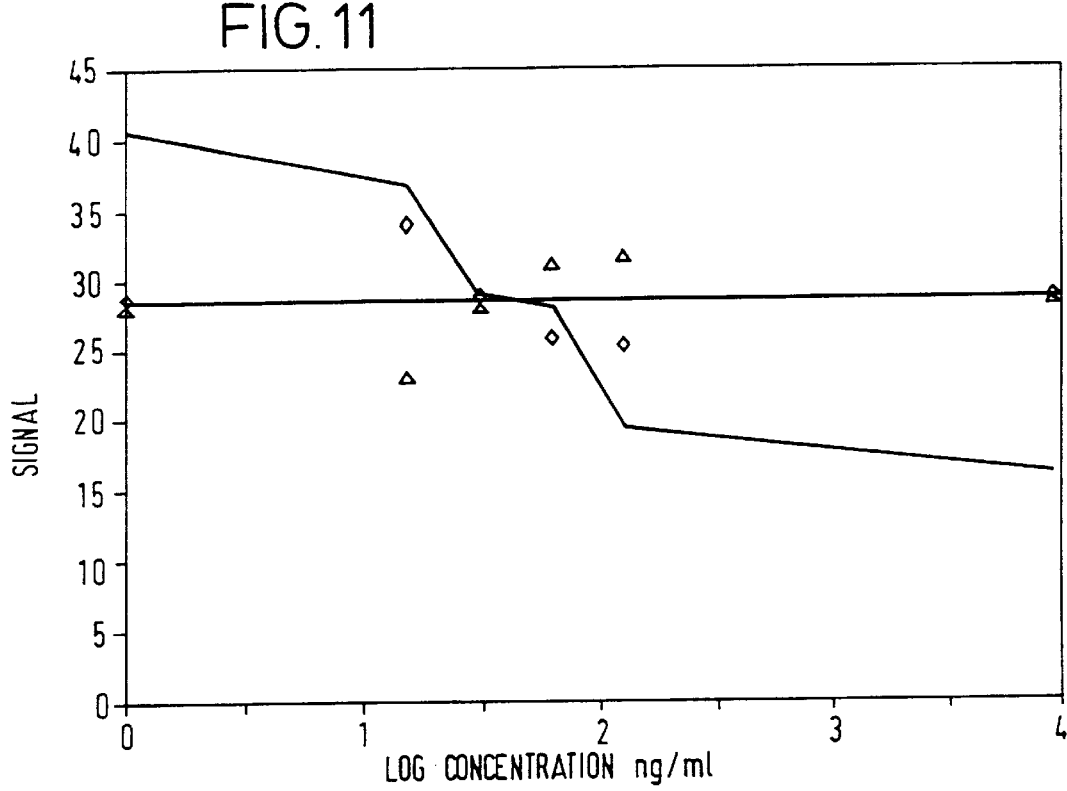
FIG. 11 is a plot of signal versus log concentration of zones IV and V in example 4.

The CFDs were filled with a range of morphine standards and read after an incubation period in a humid environment. Both zones IV and V were read after 15 minutes, although the read time for each zone can be optimised independently. Zone IV is the measurement zone, and so the signal is a measure of the analyte concentration. (FIG. 11).

The reagent in zone II is chosen to give a signal from zone V equal to the high asymptote or the cutoff position. This reference zone corrects for fluorophore signal strength and patient sample fluorescence, but is not dependent on assay performance.

One could incorporate a region to provide an assay check using zones III and VI. This could be fabricated in a similar way to the region giving a signal equal to the high asymptote in example 2.

EXAMPLE 5
1. PREPARATION OF STARTING MATERIALS 1.1 Fabrication of Antibody-coated Waveguides As for example 1 except that zone IV was treated with a premix of rat anti-mouse and mouse anti-morphine antibodies, while zones V and VI were treated with rat anti-mouse antibody only.

1.2 Preparation of Morphine Conjugated to Fluorescein Isothiocyanate (FITC)

As for example 1.

1.3 Microdosing of the Specific Reagents Over Each Discrete Reference Zone

Using the method in example 1, morphine-FITC conjugate was microdosed over zone I, a premix of morphine-FITC conjugate and mouse anti-morphine antibody over zone II and a premix of morphine and mouse anti-morphine antibody over zone III.

1.4 Fabrication of FCFD Test Devices

As for example 1.

1.5 Preparation of Morphine Standard Solutions

As for example 1.

1.6 Apparatus Used in the Measurement of the Morphine Assay

As for example 1.

2. ASSAY PROCEDURE FOR MORPHINE

The CFDs were filled with a range of morphine standards and read after incubation in a humid environment.

Zone IV was read at 15 minutes, after equilibrium had been reached. Zones V and VI need to be read after shorter incubation times, before competition of the microdosed reagents with the analyte occurs. This time is defined by the dissociation of the assay. In this example (FIG. 12), zones V and VI were read after 90 seconds.

Under these conditions, zones V and VI produce a signal equivalent to the high and low asymptote respectively, regardless of the morphine concentration in the patient sample.

Figure 13:
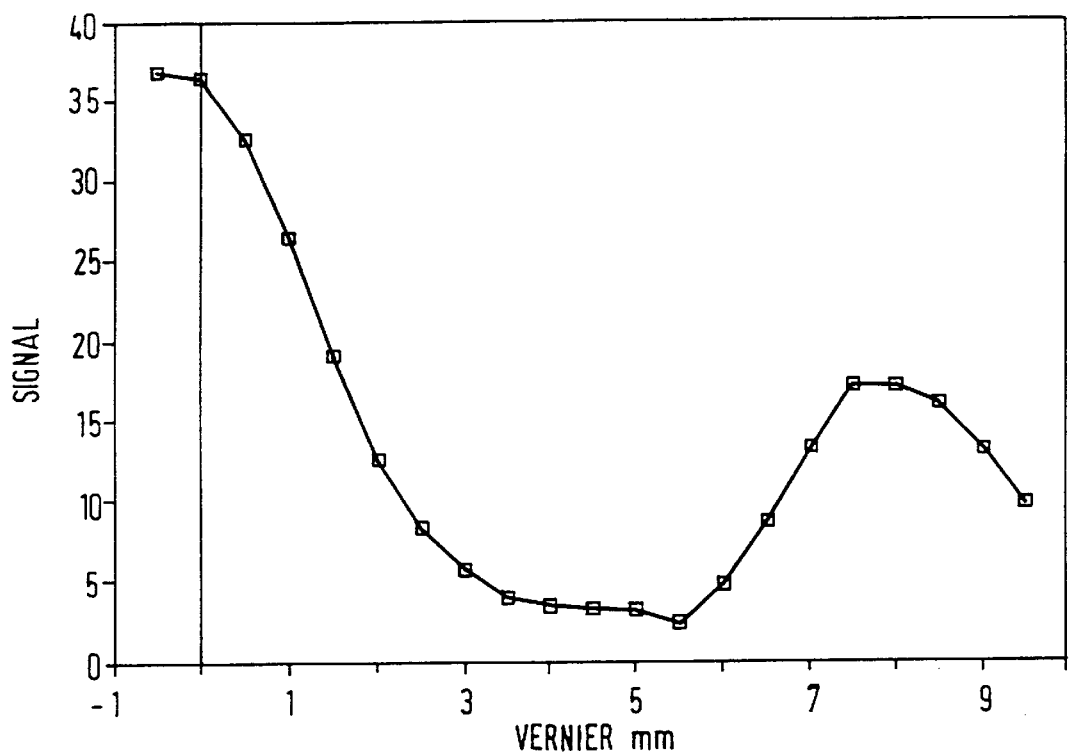
FIG. 13 is a plot of signal versus vernier distance in example 5.

FIG. 13 shows signal plotted against distance from the optical edge of the CFD. The read positions for the three zones would typically be at 1 mm, 4 mm and 8 mm.

EXAMPLE 6
1. PREPARATION OF STARTING MATERIALS 1.1 Fabrication of Antibody-coated Waveguides As for example 1, except that all zones were treated with a premix of rat anti-mouse antibody and mouse anti-morphine antibody.

1.2 Preparation of Morphine Conjugated to Fluorescein Isothiocyanate (FITC)

As for example 1.

1.3 Microdosing of the Specific Reagents Over Each Discrete Reference Zone

Zone I was fabricated as in example 1, using morphine FITC conjugate microdosed onto the plate. The specific reagents were microdosed onto the antibody-coated waveguide (as described in 1.1);

Zone VI was designed to produce a signal equivalent to the high asymptote by microdosing with morphine FITC conjugate, and zone V was microdosed with unlabelled morphine to produce a signal equivalent to the low asymptote.

1.4 Fabrication of FCFD Test Devices

As for example 1.

1.5 Preparation of Morphine Standard Solutions

As for example 1.

1.6 Apparatus Used in the Measurement of the Morphine Assay

As for example 1.

2. ASSAY PROCEDURE FOR MORPHINE

Figure 14:
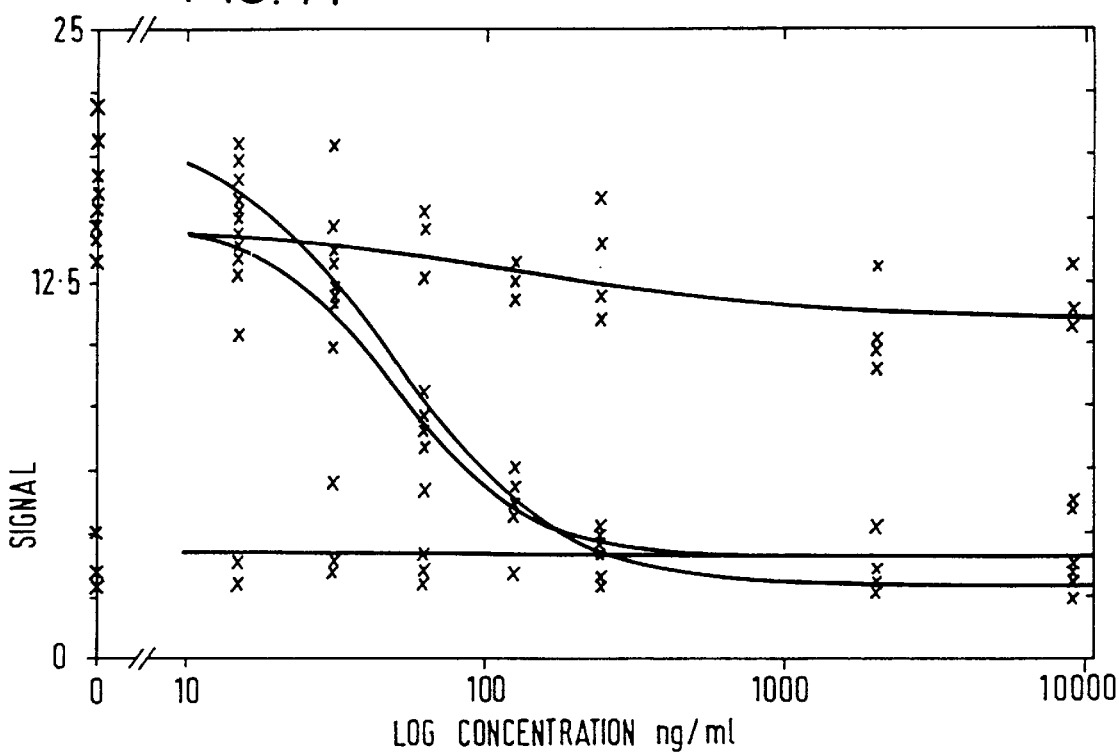
FIG. 14 is a plot of signal versus log concentration of zones IV, V and VI in example 6.
Figure 15:
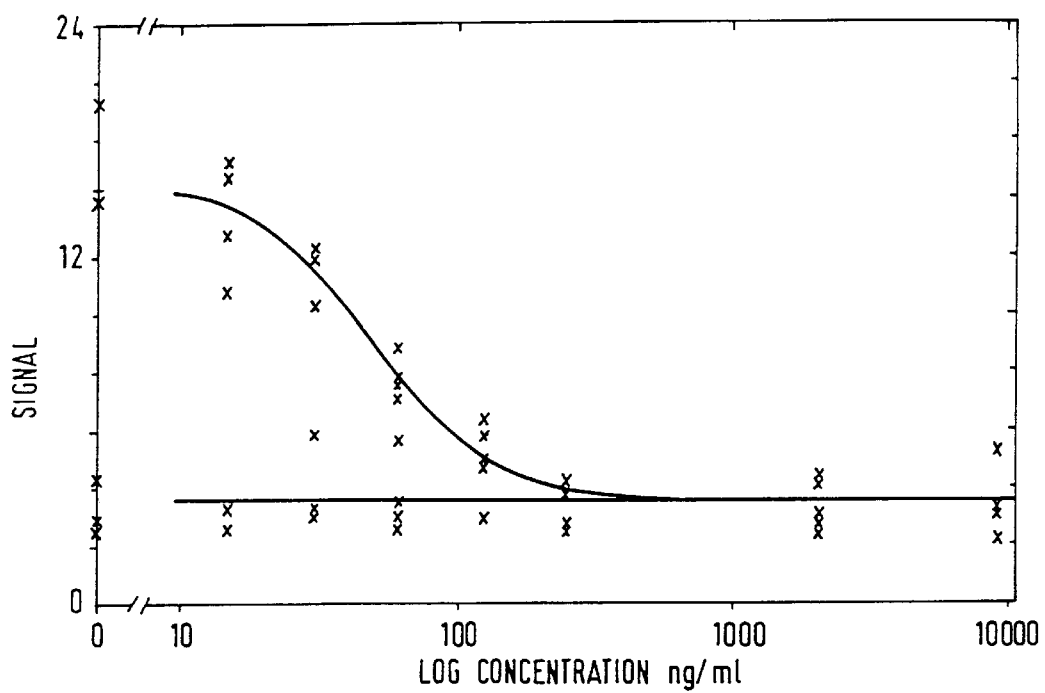
FIG. 15 is a plot of signal versus log concentration of zones IV and V in example 6.
Figure 16:
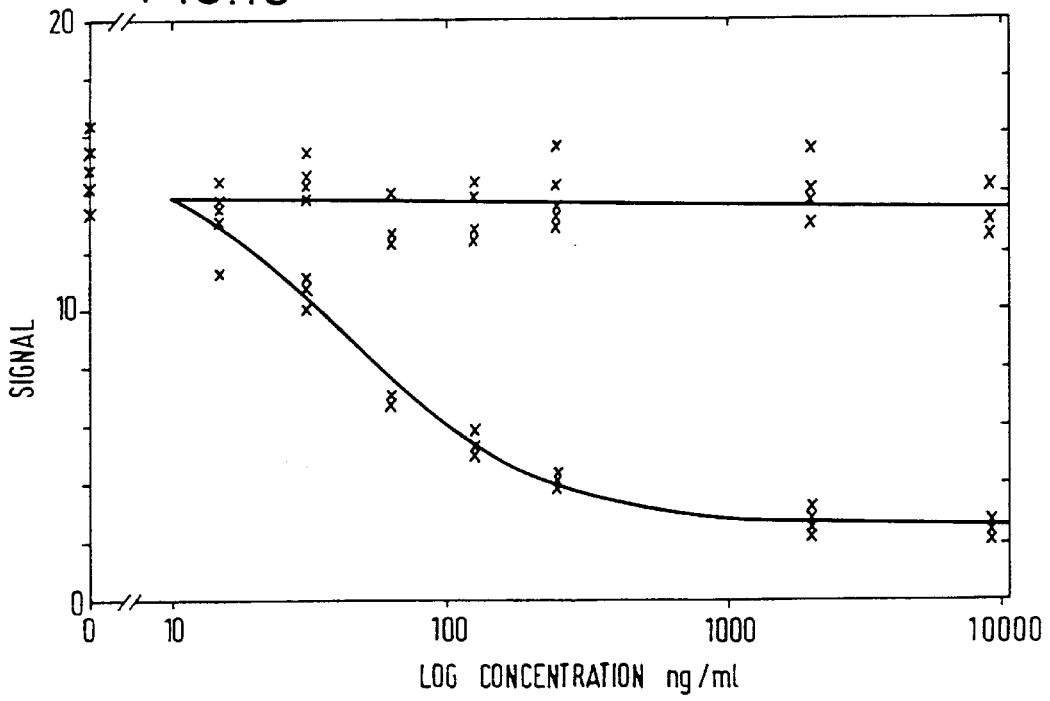
FIG. 16 is a plot of signal versus log concentration of zones V and VI in example 6.

The CFDs were filled with a range of morphine standards and read after incubation in a humid environment. Zone IV was read at 15 minutes after the assay had come to equilibrium. Zone V and VI were read after 10 seconds. The read time was chosen to enable the zones to be measured before the analyte could compete with the microdosed reagents, the time being dependent on the dissociation rate of the assay. FIG. 16 shows the data from zone IV and VI. FIG. 15 shows the data from Zone IV and V. FIG. 14 shows the data from all three zones IV, V and VI.

EXAMPLE 7
1. PREPARATION OF STARTING MATERIALS 1.1 Fabrication of Antibody-coated Waveguides As for example 1 except that zone V was treated with rat anti-mouse antibody and zone IV with a premix of rat anti-mouse and mouse anti-morphine antibody.

1.2 Preparation of Morphine Conjugated to Fluorescein Isothiocyanate (FITC)

As for example 1.

1.3 Microdosing of the Specific Reagents Over Each Discrete Reference Zone

Using the method outlined in example 1, zone I was microdosed with morphine-FITC conjugate and zone II with a premix of mouse anti-morphine antibody, morphine and morphine-FITC conjugate.

The combination of morphine and morphine FITC conjugate was used to enable zones II/V to produce a signal equal to the cutoff of the assay rather than the high or low asymptote.

1.4 Fabrication of FCFD Test Devices
As for example 1.
1.5 Preparation of Morphine Standard Solutions
As for example 1.
1.6 Apparatus Used in the Measurement of the Morphine Assay
As for example 1.

2. ASSAY PROCEDURE FOR MORPHINE

Figure 17:
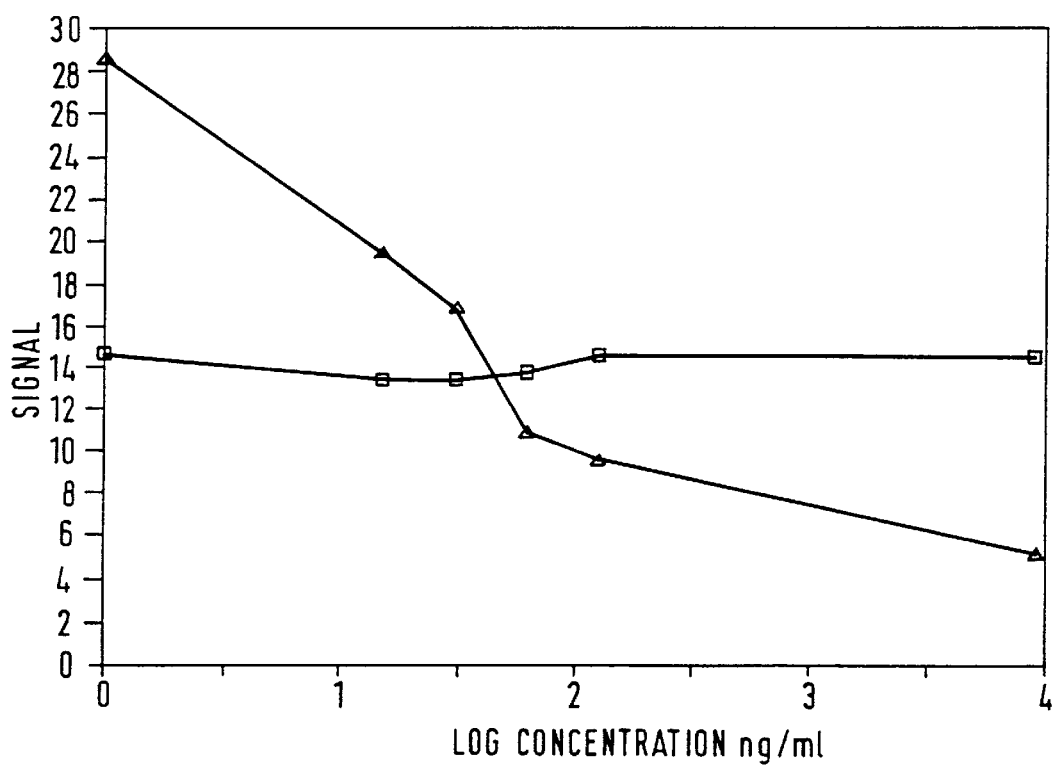
FIG. 17 is a plot of signal versus log concentration of zones IV and V in example 7.

The CFDs were filled with a range of morphine standards and read after incubation in a humid environment. Zone IV, the measurement zone, was read at 15 minutes after the assay had come to equilibrium. Zone V was read after 90 seconds. (FIG. 17). This read time was chosen to enable the signal to be read before the analyte could compete with the microdosed morphine, the time being dependent on the dissociation rate of the assay.

One could incorporate a region to provide an assay check using zones III and VI. zone III would be treated with morphine FITC conjugate and zone VI with rat anti-mouse antibody only.

The concentration of conjugate in zone III is chosen to give a signal equal to the assay's low asymptote. The conjugate used is the same as in the measurement zone, but does not bind to the plate carrying zone VI. Thus the signal is equivalent to the assay's background signal.

EXAMPLE 8

1. PREPARATION OF STARTING MATERIALS
1.1 Fabrication of Antibody-coated Waveguides
As in example 1 except that a goat anti-mouse antibody premixed with mouse anti-morphine antibody was immobilised onto zone IV of the device whilst only goat anti-mouse antibody was immobilised over the rest of the surface.
1.2 Preparation of morphine conjugated to rhodamine.
As in example 1 except that rhodamine was substituted for fluorescein.
1.3 Preparation of antibody labelled with rhodamine.
Rhodamine was conjugated to a mouse anti-morphine antibody using established techniques.
1.4 Microdosing of specific reagents over each reference zone.
As for example 1 except that zone I had only TRAP labelled morphine printed on it whilst zone II had only TRAP labelled mouse anti-morphine antibody. Zone III was not used in the example.
1.5 Preparation of morphine standard solutions
As for example 1.
1.6 Morphine samples
Urine samples containing a range of morphine concentrations were obtained and assayed using a commercially available assay prior to assay in the FCFD.
1.7 Apparatus used in the measurement of the morphine assay
As for example 1.

2. ASSAY PROCEDURE FOR MORPHINE

Assay curves were generated using eight standards in triplicate using unadulterated urine. Samples made up from the adulterated urines were assayed and their the signals obtained from the values read off the standard curve.

The reagent in zone II is chosen to give a signal equal to the cut off position. This reference zone corrects for fluorophore signal strength and patient sample fluorescence. It is also dependent on the assay performance.

No binding of sample occurs to the reagent in zone VI. Thus the signal from this region is equivalent to the assay's background signal.

The following table shows that the use of the reference zone in this assay improves the overall performance of the assay.

|  | Without Reference Zone | With Reference Zone |
| --- | --- | --- |
| Number of True negative samples | 599 | 606 |
| Number of True positive samples | 198 | 199 |
| Number of False negative samples | 12 | 11 |
| Number of False positive samples | 7 | 0 |
| % correlation overall | 97.7 | 98.7 |
| % correlation positive samples | 94.3 | 94.5 |
| % correlation negative samples | 98.8 | 100.0 |

SIGNAL PROCESSING

The previous worked examples have demonstrated various methods for measuring either the high and low asymptote or the assay's cutoff value. Various methods have then been used to correct the data from the measurement region by the calibration region data.

These methods can be summarised as either an additive, multiplicative or combined additive/multiplicative method. All methods rely on characterisation of the calibration regions during manufacture, so that any difference measured at the time of assay can be used to correct the data from the measurement region.

The most straightforward method is to directly fix the cutoff value using a calibration region. However not all proposed examples are able to achieve this and so the cutoff may be calculated from the high and low asymptote.

In FIGS. 3a to 3x, 4a to 4t and 5a to 5u, which illustrate the regions T, R and S in various embodiments of the device of FIG. 1, the symbols illustrated denote the following entities:

| | |
| --- | --- |
| ○ | Antigen under assay |
| —✱ | fluorescent label |
| ○—✱ | fluorescently labelled antigen analogue |
| □ | antigen, distinct from antigen under assay |
| —⊂ or ◇—⊂ | specific antibody to antigen under assay |
| —⊰ | specific antibody to specific antibody to antigen under assay |
| ⊢—[ or —[ | antibody non-specific to the antigen under assay |
| —▷ | specific antibody to an antibody non-specific to the antigen under assay |
| ⌒ | species to facilitate immobilisation or facilitate antibody-antigen binding |
| —⊂ | specific binding partner to the species ⌒. |

FIG. 6 shows schematically a simple fluorimetry apparatus for taking measurements from the device of FIG. 1.

FIG. 7 shows a plot of the signal obtained versus the time at which the signal is measured for zone V of a device used in the assay method described in Example 1 at two differing concentrations (0 ng/ml and 100,000 (100K) ng/ml) of morphine-3-glucuronide in the morphine standard solution.

FIG. 8 shows a plot of the signal obtained versus the log. concentration of morphine-3-glucuronide in the morphine standard solution for zone IV of a device used in the assay method described in Example 1.

FIG. 9 shows a plot of the signal obtained versus the log. concentration of morphine-3-glucuronide in the morphine standard solution for zones IV and V of a device used in the assay method described in Example 2.

FIGS. 10a and 10b show a plot of the number of positive results obtained versus the log. concentration of morphine-3-glucuronide in the morphine standard solution for the sample types described in Example 3 using a standard assay method and an assay method described in Example 3 respectively. The following symbols used in FIGS. 10a and 10b denote the sample type used: □ normal unadulterated urine ◇ urine at pH 10 Δ urine with a fluorescence level of 1 um/L + urine with a fluorescence level of 6 um/L.

FIG. 11 shows a plot of the signal obtained versus the log. concentration of morphine-3-glucuronide in the morphine standard solution for zones IV and V of a device used in the assay method described in Example 4.

Figure 12:
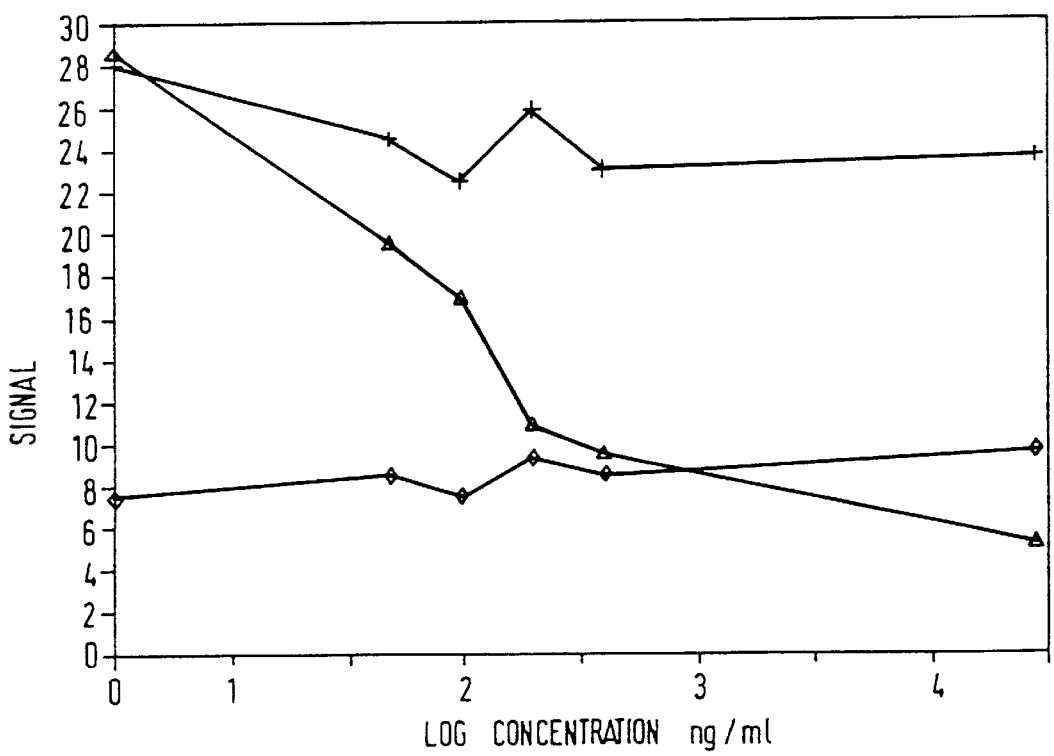
FIG. 12 is a plot of signal versus log concentration of zones IV, V and VI in example 5.

FIG. 12 shows a plot of the signal obtained versus the log. concentration of morphine-3-glucuronide in the morphine standard solution for zones IV, V and VI (denoted by the symbols Δ, + and ◇ respectively) of a device used in the assay method described in Example 5.

FIG. 13 shows a plot of the signal obtained versus the vernier distance from the optical edge of a device used in the assay method described in Example 5.

FIG. 14 shows a plot of the signal obtained versus the log. concentration of morphine-3-glucuronide in the morphine standard solution for zones IV, V and VI of a device used in the assay method described in Example 6.

FIG. 15 shows a plot of the signal obtained versus the log. concentration of morphine-3-glucuronide in the morphine standard solution for zones IV and V of a device used in the assay method described in Example 6.

FIG. 16 shows a plot of the signal obtained versus the log. concentration of morphine-3-glucuronide in the morphine standard solution for zones V and VI of a device used in the assay method described in Example 6.

FIG. 17 shows a plot of the signal obtained versus the log. concentration of morphine-3-glucuronide in the morphine standard solution for zones IV and V (denoted by the symbols Δ and ◇ respectively) of a device used in the assay method described in Example 7.

We claim:

1. A capillary-fill biosensor device suitable for use in assaying a ligand in a liquid sample, said device comprising (1) a measurement zone, (2) least one spatially distinct calibration zone and (3) at least one spatially distinct auxiliary calibration zone wherein (1) the measurement zone comprises (a) a known amount of a releasable first ancillary specific binding reagent and (b) a measurement surface comprising an immobilized measurement specific binding reagent capable of specifically binding with at least one of the ligand, the first ancillary specific binding reagent, or a first binding partner which specifically binds to said ligand and said first ancillary specific binding reagent; wherein the first ancillary specific binding reagent is provided either on a surface of the measurement zone separate from the measurement surface or prebound to said immobilized measurement specific binding partner or reagent, (2) the calibration zone comprises (c) a known amount of at least one releasable second ancillary specific binding reagent and a calibration surface comprising an immobilized calibration specific binding reagent having binding sites identical in structure to those of the immobilized measurement specific binding reagent and capable of specifically binding with at least one of the ligand, the second ancillary specific binding partner and a second binding partner which specifically binds to said ligand and said second ancillary specific binding reagent, and (3) the auxiliary calibration zone comprises an auxiliary calibration surface comprising an immobilized first auxiliary calibration binding reagent or an immobilized first auxiliary calibration reagent capable of giving rise to a zero or non-zero signal without the need for the presence of an ancillary reagent; wherein the releasable reagents remain in their respective zones without mixing with each other in the assay following either sequential or simultaneous contact with the liquid sample to provide (a) a specific binding complex immobilized on the measurement surface which is correlative of the presence or amount of the ligand in the liquid sample, (b) a calibration specific binding complex immobilized on the calibration surface as a result of an identical specific binding reaction as occurs on the measurement surface so as to provide a measurement correlative of a known amount of said ligand, and, optionally, (c) a nonspecific binding complex immobilized on the auxiliary calibration zone to provide a measurement for correcting nonspecific background binding.

2. The capillary-fill biosensor device as claimed in claim 1, wherein the auxiliary calibration zone comprises: (d) either a known amount of a releasable third ancillary specific binding reagent and a first auxiliary calibration surface comprising an immobilized first auxiliary calibration specific binding reagent having binding sites identical in structure to those of the immobilized measurement specific binding reagent and capable of specifically binding to at least one of an unknown amount of the ligand, a known amount of the ligand, and the third ancillary specific binding reagent, or (e) a first auxiliary calibration surface comprising an immobilized first auxiliary calibration nonspecific binding reagent, wherein the third ancillary specific binding reagent is provided wither on a surface of the first auxiliary calibration zone separate from the first auxiliary calibration surface or prebound to the immobilized first auxiliary calibration specific binding reagent, and is (i) an optionally labelled specific binding partner for said ligand, (ii) a labelled ligand analogue, (iii) a combination of the ligand analogue and specific binding partner for the ligand, (iv) a known amount of the ligand prebound to said specific binding partner for said ligand, (v) an optionally labelled nonspecific binding ligand which binds to the immobilizes first auxiliary calibration nonspecific binding reagent, or (vi) a combination of said nonspecific binding ligand and an optionally labelled nonspecific binding reagent therefore.

3. The device as claimed in claim 2, wherein said measurement, calibration and auxiliary calibration zones are provided as a transparent capillary comprising an upper portion and a lower portion, wherein the releasable reagents are provided on an inner surface of said upper portion and the measurement, calibration and auxiliary calibration surfaces are provided on a inner surface of said bottom portion, said transparent capillary being a light-transmissive wave guide.

4. The device as claimed in claim 1, further comprising a detection means for measuring the specific binding complex immobilized on the measurement surface, the calibration specific binding complex immobilized on the calibration surface and, optionally, the nonspecific binding complex immobilized on the auxiliary calibration zone.

5. The device as claimed in claim 4, wherein the detection means is a fluorescence monitor, the releasable reagents are labelled with a fluorogenic label, and wherein the device further comprises a radiation source for exciting said fluorogenic label.

6. The device as claimed in claim 1, wherein the first auxiliary calibration zone comprises: (e) either a known amount of releasable third ancillary specific binding reagent and a first auxiliary calibration surface comprising an immobilized first auxiliary calibration specific binding reagent having binding sites identical in structure to those of the immobilized measurement specific binding reagent and capable of specifically binding to at least one of the ligand and the third ancillary specific binding reagent, or (f) a first auxiliary calibration surface comprising an immobilized first auxiliary calibration nonspecific binding reagent, wherein the third ancillary specific binding reagent is provided either on a surface of the first auxiliary calibration zone separate from the first auxiliary calibration surface or prebound to the immobilized first auxiliary calibration specific binding reagent, and is (i) said labelled ligand analogue or (ii) said combination of the labelled ligand analogue and specific binding partner for the ligand or (iii) an optionally labelled nonspecific binding ligand which binds to the immobilized first auxiliary calibration nonspecific binding reagent.

7. The device as claimed in claim 1, wherein the auxiliary calibration zone comprises: (e) either a known amount of at least one releasable third ancillary specific binding reagent and a first auxiliary calibration surface comprising an immobilized first auxiliary calibration specific binding reagent having binding sites identical in structure to those of the immobilized measurement specific binding reagent and capable of specifically binding to at least one of the ligand and the third ancillary specific binding reagents, or (f) a first auxiliary calibration surface comprising an immobilized first auxiliary nonspecific binding reagent, wherein the third ancillary specific binding reagent is provided wither on a surface of the first auxiliary calibration zone separate from the first auxiliary calibration surface or prebound to the immobilized first auxiliary calibration specific binding reagent, and is (i) said ligand analogue or (ii) said specific binding partner for the ligand or (iii) a nonspecific binding ligand which binds to the immobilized first auxiliary nonspecific binding reagent.

8. The device as claimed in claim 1, wherein the first auxiliary calibration zone comprises: (e) either a known amount of a releasable third ancillary specific binding reagent and a first auxiliary calibration surface comprising an immobilized first auxiliary calibration specific binding reagent having binding sites identical in structure to those of the immobilized measurement specific binding reagent and capable of specifically binding to at least one of an unknown amount of the ligand, a known amount of the ligand, and the third ancillary specific binding reagent, or (f) a first auxiliary calibration surface comprising an immobilized first auxiliary calibration nonspecific binding reagent, wherein the third ancillary specific binding reagent is provided either on a surface of the first auxiliary calibration zone separate from the first auxiliary calibration surface or prebound to the immobilized first auxiliary calibration specific binding reagent, and is (i) a labelled specific binding partner for said ligand, (ii) a known amount of the ligand prebound to said specific binding partner for said ligand, (iii) an optionally labelled nonspecific binding ligand which binds to the immobilized first auxiliary calibration nonspecific binding reagent, or (iv) a combination of said nonspecific binding ligand and an optionally labelled nonspecific binding reagent therefore.

9. The device as claimed in claim 3, further comprising a layer of light-absorbing or opaque material coating an outer surface of said bottom portion of said capillary opposite the measurement, calibration and auxiliary calibration surfaces.

* * * * *